(12) United States Patent
Brounstein et al.

(10) Patent No.: US 7,329,253 B2
(45) Date of Patent: Feb. 12, 2008

(54) SUCTION SLEEVE AND INTERVENTIONAL DEVICES HAVING SUCH A SUCTION SLEEVE

(75) Inventors: Daniel M. Brounstein, Fremont, CA (US); Sean C. Daniel, Foster City, CA (US); Meir H. Moshe, El Sobrante, CA (US); Scott C. Anderson, Sunnyvale, CA (US); James W. Vetter, Portola Valley, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 525 days.

(21) Appl. No.: 10/732,670

(22) Filed: Dec. 9, 2003

(65) Prior Publication Data

US 2005/0124986 A1 Jun. 9, 2005

(51) Int. Cl.
*A61B 18/18* (2006.01)

(52) U.S. Cl. .................................................. 606/41
(58) Field of Classification Search ............... 606/39, 606/27–52; 600/564; 604/22

See application file for complete search history.

(56) References Cited

U.S. PATENT DOCUMENTS

| | | | |
|---|---|---|---|
| 1,813,902 A | | 7/1931 | Bovie |
| 2,816,552 A | | 12/1957 | Hoffman |
| 3,320,957 A | | 5/1967 | Sokolik |
| 3,375,828 A | * | 4/1968 | Sheridan ............... 604/119 |
| 3,732,858 A | | 5/1973 | Banko |
| 3,749,085 A | | 7/1973 | Willson |
| 3,910,279 A | | 10/1975 | Okada et al. |
| 3,955,578 A | | 5/1976 | Chamness et al. |
| 4,099,518 A | | 7/1978 | Baylis et al. |
| 4,245,653 A | | 1/1981 | Weaver |
| 4,347,846 A | | 9/1982 | Dormia |
| 4,451,257 A | * | 5/1984 | Atchley ............... 604/119 |
| 4,611,594 A | | 9/1986 | Grayhack |
| 4,650,466 A | | 3/1987 | Luther |
| 4,808,154 A | * | 2/1989 | Freeman ............... 604/22 |
| 4,890,611 A | | 1/1990 | Monfort |
| 4,903,696 A | | 2/1990 | Stasz et al. |

(Continued)

FOREIGN PATENT DOCUMENTS

DE 195 28 440 A1 2/1997

(Continued)

OTHER PUBLICATIONS

International Search Report mailed May 22, 2006, In International Application No. PCT/US04/40436.

(Continued)

*Primary Examiner*—Roy D. Gibson
*Assistant Examiner*—Pete Vrettakos
(74) *Attorney, Agent, or Firm*—Young Law Firm, P.C.

(57) ABSTRACT

A suction sleeve is configured to couple to the shaft of an RF device to evacuate hot gasses, fluids and/or other aspirates. The suction sleeve may be configured to be disposed coaxially around the shaft between the first end of the shaft and the work element (e.g., an RF cutting element) thereof. The suction sleeve defines a suction port and a plurality of openings near the work element, and is configured to enable suction in through the plurality of openings and out through the suction port.

44 Claims, 13 Drawing Sheets

U.S. PATENT DOCUMENTS

| | | | |
|---|---|---|---|
| 4,966,604 | A | 10/1990 | Reiss |
| 5,071,424 | A | 12/1991 | Reger |
| 5,083,570 | A | 1/1992 | Mosby |
| 5,100,423 | A | 3/1992 | Fearnot |
| 5,147,355 | A | 9/1992 | Friedman et al. |
| 5,152,293 | A | 10/1992 | Vonesh et al. |
| 5,156,610 | A | 10/1992 | Reger |
| 5,174,296 | A | 12/1992 | Watanabe et al. |
| 5,176,688 | A | 1/1993 | Narayan |
| 5,181,916 | A | 1/1993 | Reynolds et al. |
| 5,192,291 | A | 3/1993 | Pannek |
| 5,203,773 | A | 4/1993 | Green |
| 5,211,651 | A | 5/1993 | Reger |
| 5,217,451 | A | 6/1993 | Freitas |
| 5,217,479 | A | 6/1993 | Shuler |
| 5,224,488 | A | 7/1993 | Neuffer |
| 5,224,944 | A | 7/1993 | Elliott |
| 5,224,945 | A | 7/1993 | Pannek et al. |
| 5,234,428 | A | 8/1993 | Kaufman |
| 5,282,484 | A | 2/1994 | Reger |
| 5,308,321 | A | 5/1994 | Castro |
| 5,318,565 | A | 6/1994 | Kuriloff et al. |
| 5,318,576 | A | 6/1994 | Plassche |
| 5,325,860 | A | 7/1994 | Seward et al. |
| 5,415,656 | A | 5/1995 | Tihon et al. |
| 5,441,510 | A | 8/1995 | Simpson et al. |
| 5,460,602 | A | 10/1995 | Shapira |
| 5,527,326 | A | 6/1996 | Hermann |
| 5,554,163 | A | 9/1996 | Shturman |
| 5,630,426 | A | 5/1997 | Eggers et al. |
| 5,632,754 | A | 5/1997 | Farley et al. |
| 5,672,172 | A | 9/1997 | Zupkas |
| 5,709,697 | A | 1/1998 | Ratcliff |
| 5,722,949 | A | 3/1998 | Sanese |
| 5,766,191 | A | 6/1998 | Trerotola |
| 5,794,626 | A | 8/1998 | Kieturakis |
| 5,800,431 | A | 9/1998 | Brown |
| 5,830,214 | A | 11/1998 | Flom et al. |
| 5,895,399 | A | 4/1999 | Barbut et al. |
| 5,913,855 | A | 6/1999 | Gough et al. |
| 5,928,159 | A | 7/1999 | Eggers et al. |
| 5,928,164 | A | 7/1999 | Burbank |
| 5,947,964 | A | 9/1999 | Eggers et al. |
| 5,954,655 | A | 9/1999 | Hussman |
| 5,954,670 | A | 9/1999 | Baker |
| 5,964,755 | A * | 10/1999 | Edwards ............... 606/41 |
| 5,976,129 | A | 11/1999 | Desai |
| 6,007,555 | A * | 12/1999 | Devine ............... 606/169 |
| 6,015,390 | A | 1/2000 | Krag |
| 6,022,362 | A | 2/2000 | Lee |
| 6,036,708 | A | 3/2000 | Sciver |
| 6,063,082 | A | 5/2000 | DeVore |
| 6,080,149 | A | 6/2000 | Huang |
| 6,080,151 | A | 6/2000 | Swartz et al. |
| 6,096,053 | A | 8/2000 | Bates |
| 6,099,534 | A | 8/2000 | Bates |
| 6,106,524 | A | 8/2000 | Eggers et al. |
| 6,110,170 | A | 8/2000 | Taylor et al. |
| 6,179,860 | B1 | 1/2001 | Fulton, III et al. |
| 6,221,006 | B1 | 4/2001 | Dubrul et al. |
| 6,238,389 | B1 | 5/2001 | Paddock et al. |
| 6,238,393 | B1 | 5/2001 | Mulier et al. |
| 6,254,591 | B1 | 7/2001 | Roberson |
| 6,258,088 | B1 | 7/2001 | Tzonev et al. |
| 6,280,450 | B1 | 8/2001 | McGuckin, Jr. |
| 6,325,797 | B1 | 12/2001 | Stewart et al. |
| 6,331,166 | B1 | 12/2001 | Burbank |
| 6,387,056 | B1 | 5/2002 | Kieturakis |
| 6,423,081 | B1 | 7/2002 | Lee et al. |
| 6,440,147 | B1 | 8/2002 | Lee et al. |
| 6,447,443 | B1 | 9/2002 | Keogh et al. |
| 6,453,906 | B1 | 9/2002 | Taylor et al. |
| 6,514,248 | B1 | 2/2003 | Eggers et al. |
| 6,530,924 | B1 | 3/2003 | Ellman et al. |
| 6,547,724 | B1 | 4/2003 | Soble et al. |
| 6,602,204 | B2 | 8/2003 | Dubrul et al. |
| 6,605,047 | B2 | 8/2003 | Zarins et al. |
| 6,689,145 | B2 | 2/2004 | Lee et al. |
| 6,702,831 | B2 | 3/2004 | Lee et al. |
| 6,706,039 | B2 * | 3/2004 | Mulier et al. ............... 606/41 |
| 6,712,757 | B2 | 3/2004 | Becker et al. |
| 6,725,862 | B2 | 4/2004 | Klinberg et al. |
| 6,890,295 | B2 * | 5/2005 | Michels et al. ............. 600/114 |
| 2001/0047169 | A1 | 11/2001 | McGuckin, Jr. |
| 2002/0058885 | A1 | 5/2002 | Burbank et al. |

FOREIGN PATENT DOCUMENTS

| | | |
|---|---|---|
| DE | 197 06 751 A1 | 2/1997 |
| EP | 0 472 368 B1 | 2/1992 |
| EP | 0 829 232 A2 | 3/1998 |
| EP | 0 829 232 A3 | 3/1998 |
| EP | 0 908 156 B1 | 11/2003 |
| FR | 2 275 226 | 5/1975 |
| GB | 1 331 468 | 9/1973 |
| GB | 2 204 496 A | 11/1988 |
| GB | 2 311 468 A | 1/1997 |
| NL | 1.004723 | 9/1912 |
| SU | 1235497 A1 | 6/1986 |
| SU | 1355266 A1 | 11/1987 |
| WO | WO 92/20291 | 11/1992 |
| WO | WO 95/02370 | 1/1995 |
| WO | WO 95/02371 | 1/1995 |
| WO | WO 96/29946 | 10/1996 |
| WO | WO 98/08441 | 3/1998 |
| WO | WO 99/01074 | 1/1999 |
| WO | WO 99/04704 | 2/1999 |
| WO | WO 99/43262 | 9/1999 |
| WO | WO 99/44506 | 10/1999 |
| WO | WO 99/53851 | 10/1999 |
| WO | WO 00/10471 | 3/2000 |
| WO | WO 00/12009 | 3/2000 |
| WO | WO 00/16697 | 3/2000 |
| WO | WO 00/30531 | 6/2000 |
| WO | WO 00/33743 | 6/2000 |
| WO | WO 00/44295 | 8/2000 |
| WO | WO 00/45854 | 8/2000 |
| WO | WO 00/74561 A1 | 12/2000 |
| WO | WO 01/28445 A1 | 4/2001 |
| WO | WO 01/28446 A1 | 4/2001 |

OTHER PUBLICATIONS

Written Opinion mailed May 22, 2006, in International Application No. PCT/US04/40436.

* cited by examiner

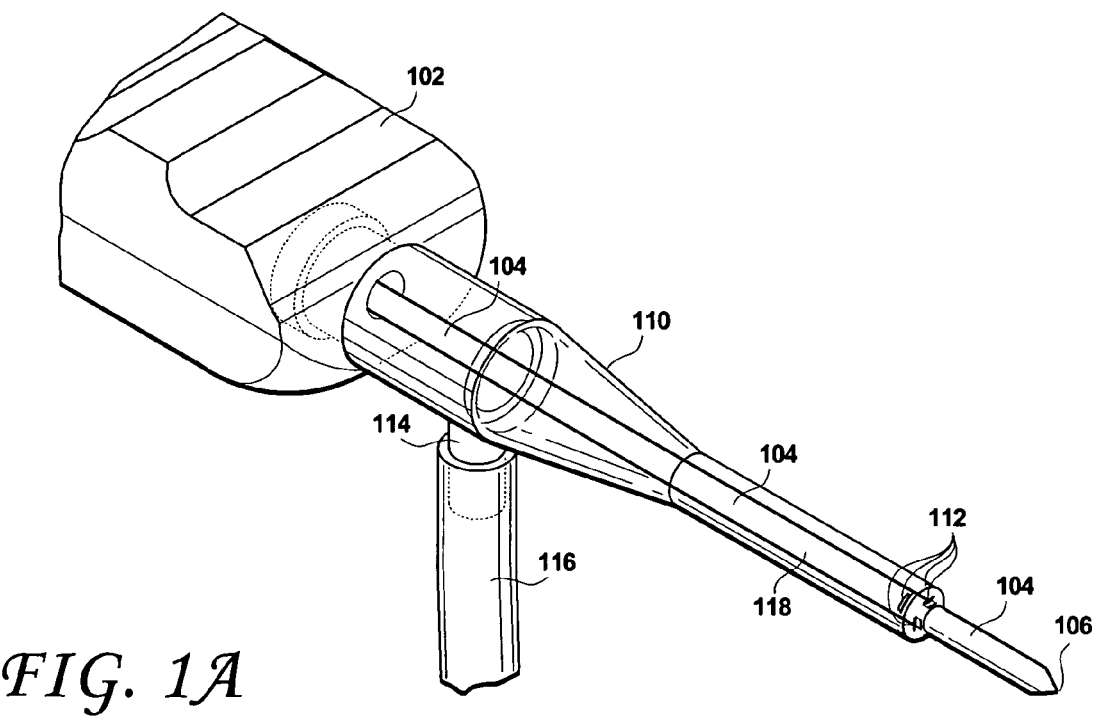
FIG. 1A
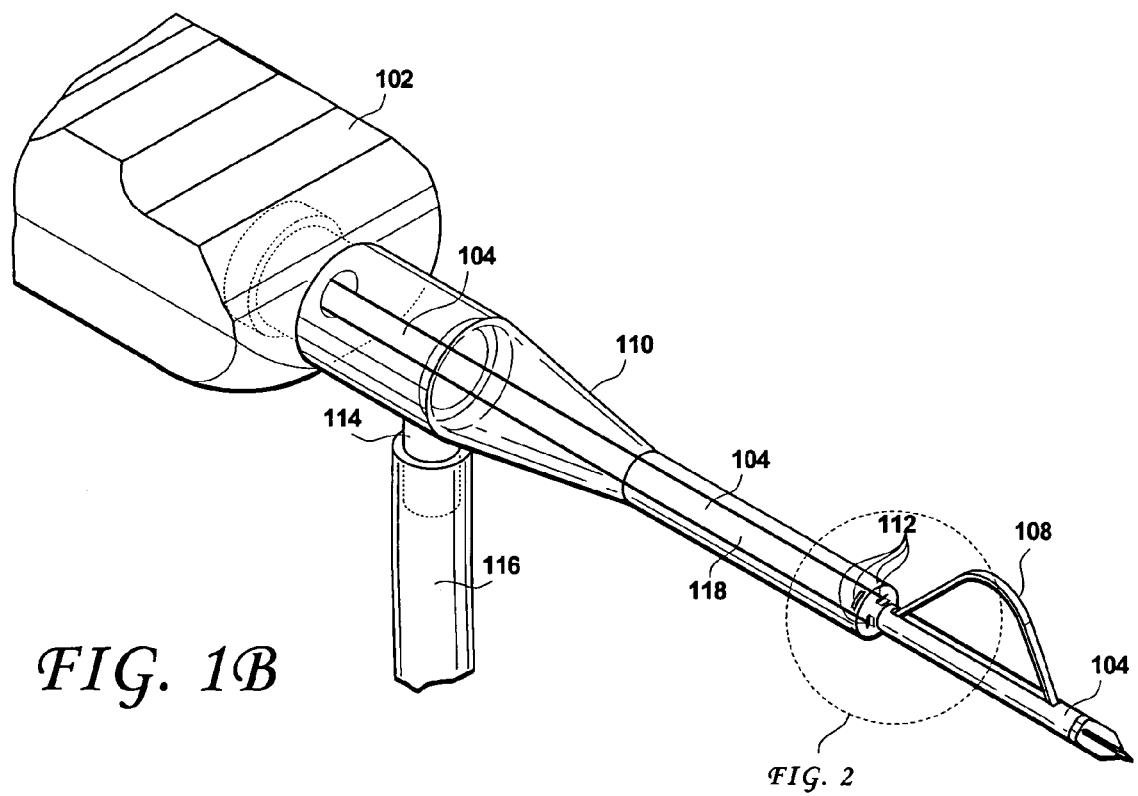
FIG. 1B
FIG. 2

SUCTION SLEEVE AND INTERVENTIONAL DEVICES HAVING SUCH A SUCTION SLEEVE

BACKGROUND OF THE INVENTION

1. Field of the Invention

The present invention relates to the field of electrosurgery. In particular, the present invention relates to suction sleeves for electrosurgical devices for the evacuation of hot gasses, bodily fluids and other aspirates from an electrosurgical site.

2. Description of the Related Information

In use, electrosurgical instruments generate a great deal of heat at and around the RF cutting element of the instrument. All of the RF energy applied to the device is typically concentrated at the distal cutting element of the device, which consequently experiences a high current density. This high current density creates an arc between the targeted tissue and the cutting element of the device, which arc cuts the targeted tissue by vaporization of the cells that come into contact with the arc. This arc also creates very high temperatures. As the cells are vaporized, hot gasses (such as steam and smoke, for example) are created. Moreover, when arterial blood or other fluids fill the cavity around the cutting element of the electrosurgical element, these fluids are rapidly heated.

The presence of such hot gasses has several adverse consequences. First among these adverse consequences is thermal damage to the otherwise viable and healthy tissue surrounding the electrosurgical site. Second, the presence of heated fluids may also adversely affect the operation of the RF device itself. As the fluids come into contact with the RF cutting element of the electrosurgical device, the arc generated within the gap between the targeted tissue and the distal RF tip of the device may be lost. In turn, this loss of arc results in a decrease in the current density at the cutting element of the device, which current is then redistributed over the comparatively greater surface area of the distal region of the RF device. Indeed, instead of the RF energy being concentrated in the very small area of the cutting element (e.g., cutting blade or tip) of the device (which leaves adjacent areas relatively unaffected by the great temperatures generated at the arc), the applied RF energy is spread out over the greater surface of the distal region of the RF device, thereby heating the entire cavity. This heating, in addition to causing unintended thermal damage to adjacent tissue and structures, may also damage the biopsy specimen, destroying the architecture of the severed tissue and hampering histopathological examination thereof. Moreover, the heat generated at the cutting element of the device may also transfer to the shaft of the device, even during a procedure of relatively short duration.

To reduce the unintended thermal damage to adjacent tissues, it is necessary to evacuate the hot gasses and fluids from the electrosurgical site. Doing so in an efficient manner reduces the internal temperature of the cavity within which the RF procedure is being carried out, and reduces thermal damage to adjacent tissues. Moreover, efficient evacuation of gasses, fluids and smoke facilitates the re-initiation of the RF arc by re-creating the gap between the targeted tissue and the RF tip.

From the foregoing, it is apparent that evacuation of hot gasses and fluids is essential to prevent unintended thermal damage to adjacent tissue structures and to insure the maintenance of the RF arc at the distal tip of the electrosurgical device. What are needed, therefore, are devices for evacuation of heated gasses and fluids from an RF electrosurgery site. Such devices should efficiently remove both heated gasses and fluids without, however, unduly increasing the size of the device near the distal tip of the device. Such a device, moreover, should not hamper the physician as he or she manipulates (e.g., rotates) the electrosurgical device during the procedure. Ideally, such device should also be configured such that tissue coming into contact with it does not block the evacuation of the heated gasses and fluids.

SUMMARY OF THE INVENTION

The present invention, according to an embodiment thereof, is a soft tissue interventional device, including a handle; a shaft defining a first end and a second end, the first end being coupled to the handle; a work element coupled to the second end of the shaft, and a suction sleeve disposed coaxially around the shaft between the first end of the shaft and the work element, the suction sleeve defining a suction port and a plurality of openings near the work element, the suction sleeve being configured to enable suction in through the plurality of openings and out through the suction port.

The suction sleeve may define a circumference around the shaft and the plurality of openings may be defined around the circumference of the suction sleeve. The plurality of openings may overlap around the circumference of the suction sleeve. The suction sleeve may define a first external surface and a second external surface disposed at a non-zero angle relative to first external surface, and at least one of the plurality of openings may be defined within the first external surface and at least one of the plurality of openings may be defined within the second external surface. At least one of the plurality of openings defined within the first external surface may overlap in extent with at least one of the plurality of openings defined within the second external surface. One or more of the plurality of openings may define a generally cloverleaf shape. The suction port may be defined within the suction sleeve adjacent the first end of the shaft. The suction sleeve may be configured to be freely rotatable about the shaft. The sleeve may include an internal surface that may define an interior sleeve lumen dimensioned so as to allow the shaft to freely rotate therethrough. The plurality of openings may be open to the interior sleeve lumen. The interior sleeve lumen may be dimensioned so as to allow free passage of aspirates through the plurality of openings and out the suction port. The work element may be configured to cut soft tissue. The work element may be energizable with RF energy. The suction sleeve may be configured to be removable from the shaft. The suction sleeve may be configured to be positioned on the shaft without decoupling the shaft from the handle. The suction sleeve may be at least partially transparent. The sleeve may comprise a first portion and a second portion, the second portion being configured to slide coaxially relative to the first portion to assume a first position in which the sleeve has a first length and second positions in which the length of the sleeve is greater than the first length. The second portion may telescope (e.g., slide axially) relative to the first portion.

Another embodiment of the present invention is a suction sleeve for a soft tissue interventional device that includes a shaft that includes a tapered portion defining a predetermined extent, the tapered portion defining a first external surface and a first internal surface, the first internal surface defining an internal axial lumen spanning the predetermined extent, the internal axial lumen being configured to receive the shaft, the first external surface defining a suction port and a plurality of openings that open to the internal axial lumen.

The tapered portion may define a second external surface disposed at a non-zero angle relative to the first external surface and both the first and second external surfaces may define openings that open to the internal axial lumen. The openings defined within the first external surface may overlap with the openings defined within the second external surface. The plurality of openings may be shaped and dimensioned so as to enable free passage of aspirates (smoke, heated fluids, gasses, for example) from a cavity within soft tissue through the internal axial lumen and out through the suction port. One or more of the plurality of openings may define a generally cloverleaf shape. The suction sleeve may be at least partially transparent. The tapered portion may include a first sleeve half and a second sleeve half, the first sleeve half being configured to mate with the second sleeve half. The suction sleeve may further include at least one integral hinge bridging the first sleeve half to the second sleeve half. The tapered portion may include at least one sleeve mating assembly. The at least one sleeve mating assembly may be configured to removably mate the first sleeve half to the second sleeve half. The sleeve may include a first portion and a second portion, the second portion being configured to slide coaxially with the first portion to assume a first position in which the sleeve has a first length and second positions in which the length of the sleeve is greater than the first length. The second portion telescopes (e.g., slide axially) within or relative to the first portion.

The present invention, according to yet another embodiment thereof, is a method for cutting a specimen of soft tissue, comprising the steps of providing a device including a handle, a shaft coupled to the handle and defining a first end and a second end, a cutting element coupled to the second end of the shaft, and a suction sleeve disposed coaxially around the shaft between the first end of the shaft and the cutting element, the suction sleeve defining a suction port and a plurality of openings near the work element, the suction sleeve being configured to enable suction in through the plurality of openings and out through the suction port; inserting the device in the soft tissue; cutting the tissue specimen using the cutting element, and applying suction to the suction port during the cutting step.

The cutting element may be energizable with RF energy and the cutting step may include a step of applying RF energy to the cutting element.

BRIEF DESCRIPTION OF THE DRAWINGS

FIG. 1A is a perspective view of a suction sleeve according to an embodiment of the present invention, coupled to an exemplary excisional device.

FIG. 1B is a perspective view of the suction sleeve of FIG. 1, coupled to another exemplary excisional device.

DETAILED DESCRIPTION

Figure 2:
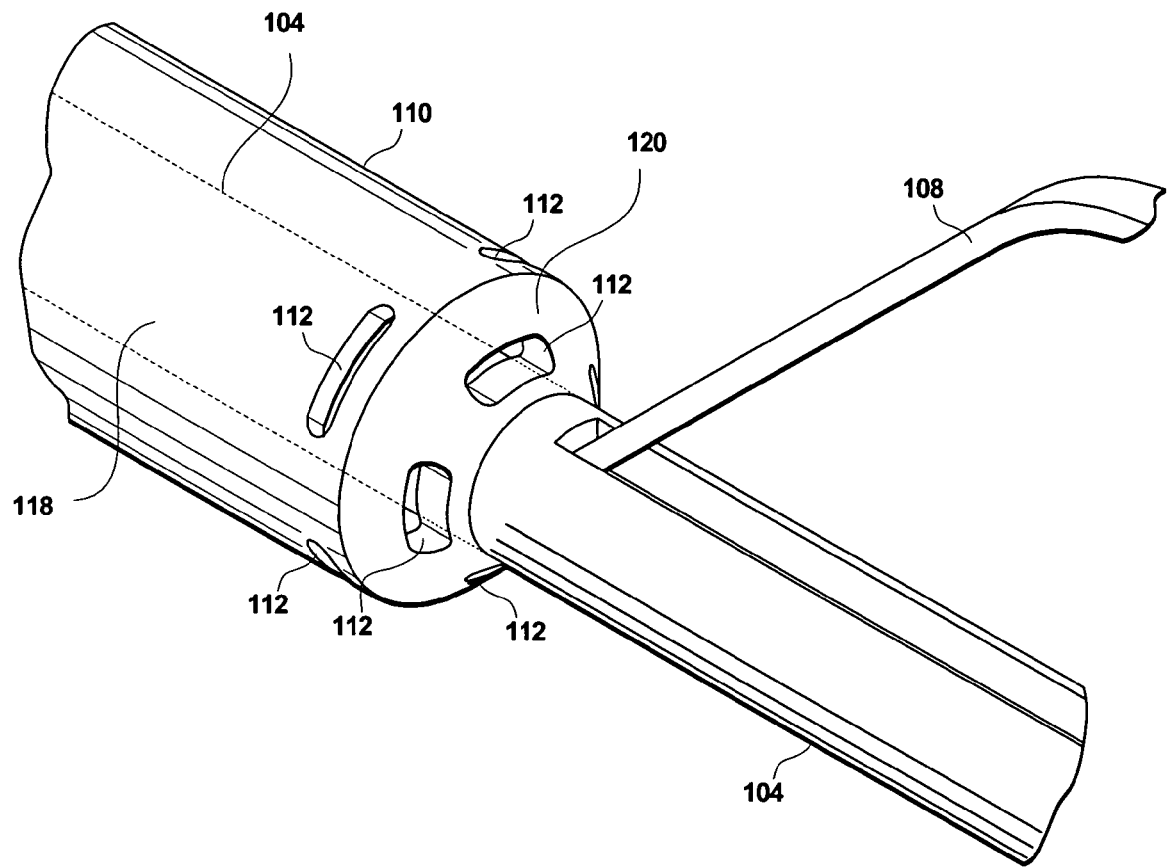
FIG. 2 is a detail view of the distal end of the RF device of FIG. 1B, to illustrate an exemplary configuration of the distal openings of the suction sleeve, according to an embodiment of the present invention.

FIG. 1A is a perspective view of a suction sleeve 110 according to an embodiment of the present invention, coupled to an exemplary excisional device. For simplicity of illustration, only the distal portion of the excisional device is shown. The handle of the excisional device is shown at 102. A shaft 104 extends from the handle 102 and defines a distal tip 106. When energized by an RF source, an arc develops between the distal tip 106 and the targeted tissue. Such a device is also called a Bovie pencil. When RF energy is applied, an arc develops at the tip 106, and cutting of the tissue occurs by vaporization of the tissue that comes into contact with the RF arc. FIG. 1B shows the suction sleeve 110 coupled to another electrosurgical device. In this case, the electrosurgical cutting element 108 includes a wire loop that is configured to bow and extend away from the shaft 104 and to retract back toward the shaft 104. As detailed above, hot gasses and fluids are frequently present at the electrosurgical site. To evacuate such heated gasses and fluids (including smoke, blood and intercellular fluids, for example), the excisional devices of FIGS. 1A and 1B (as well as other types of electrosurgical devices) may be equipped with a suction sleeve according to one of the embodiments of the present invention.

The suction sleeve 110 is disposed coaxially around the shaft 104 between the proximal end of the shaft 104 (i.e., closest to the handle 102 of the device) and the cutting element (in this case, the distal tip 106 or the loop 108 of the shaft 104). As shown, the suction sleeve 110 may surround at least a portion of the shaft 104 and define a first external surface 118 and a first internal surface 122 (best shown in FIG. 7). The first internal surface 122 faces the shaft 104 and defines an internal lumen 124 through which the shaft 104 is or may be inserted.

To enable the evacuation of hot gasses, fluids and/or other aspirates, the suction sleeve 110 defines a plurality of openings 112 at and/or near the distal end of the suction sleeve 110 (i.e., that end of the suction sleeve 110 that is closest to the RF cutting element), as well as a suction port 114 at or near the proximal end of the sleeve (i.e., that end of the sleeve 110 that is closest to the handle 102). When suction is applied to the suction port 114, the suction sleeve 110 enables suction of gasses, fluids and/or aspirates in through the plurality of openings 112 and out through the suction port 114. The suction sleeve 110 may be fixedly attached to the electrosurgical device in such a manner that it rotates along with the shaft 104. Alternatively, the suction sleeve 110 may be attached so as to enable its free rotation about and independent of the shaft 104. That is, the shaft 104 may be rotated within a stationary suction sleeve 110 or the suction sleeve may be manipulated so as to rotate it about a stationary shaft 104. When the suction sleeve 110 is coupled to the electrosurgical device in such a manner as to allow its free rotation about the shaft 104, the physician is free to manipulate and rotate the RF device during a procedure as needed without causing a corresponding rotation in the suction sleeve and the vacuum line 116 attached to the suction port 114.

FIG. 2 is a detail view of the distal end of the RF device of FIG. 1B, to illustrate an exemplary configuration of the distal openings of the suction sleeve, according to an embodiment of the present invention. As shown, the suction sleeve 110 may define a first external surface 118 and a second external surface 120 disposed at a non-zero angle relative to first external surface 118. As shown in FIG. 2, the first and second external surfaces 118 and 120 together may give the distal end of the suction sleeve 110 a tapered appearance, to facilitate entry thereof into soft tissue.

Figure 3:
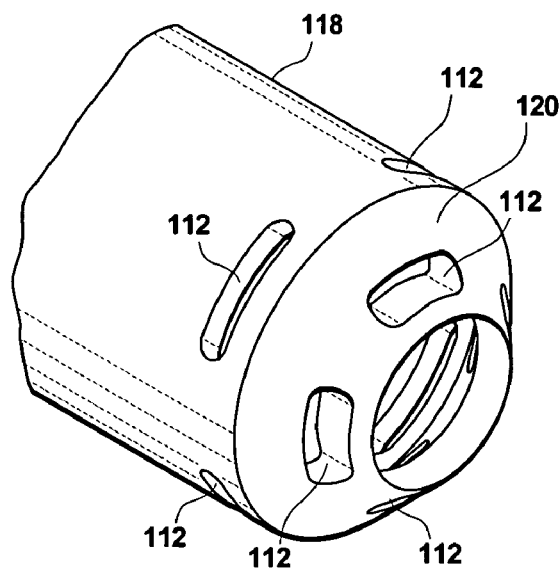
FIG. 3 is a perspective view of the distal end of the suction sleeve of FIGS. 1A-5, illustrating the overlapping nature of the openings therein.
Figure 4:
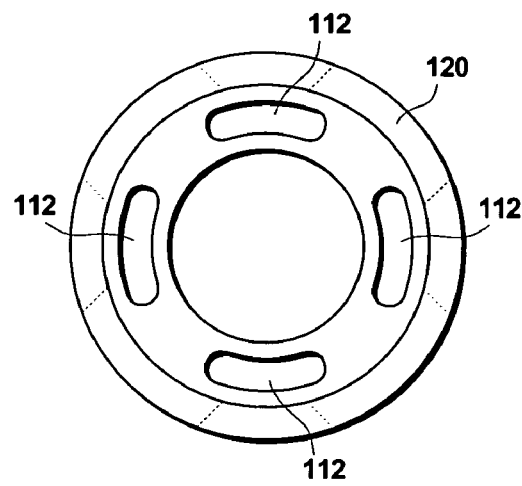
FIG. 4 is a front view of the distal end of the suction sleeve of FIGS. 1A-6.
Figure 5:
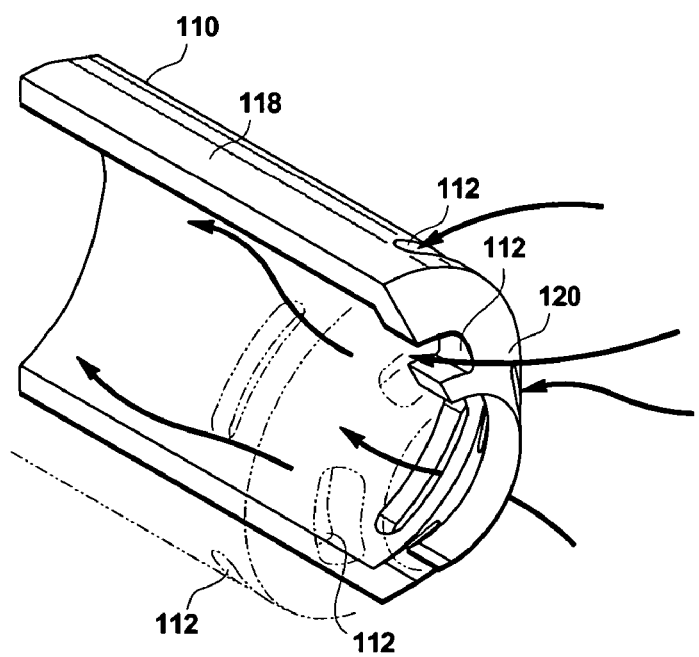
FIG. 5 is a perspective cutaway view of the distal end of the suction sleeve of the embodiment of the suction sleeve of FIGS. 1A-4, illustrating the manner in which smoke, fluids and/or other aspirates may be suctioned into the present suction sleeve.

To enable evacuation of hot gasses and fluids, the first and/or second surfaces 118, 120 may define a plurality of openings 112. Referring now collectively to FIGS. 3, 4 and 5, at least one of the plurality of openings 112 may be defined within the first external surface 118 and at least one of the plurality of openings 112 may be defined within the second external surface 120. In the embodiment of FIG. 2, a plurality of openings 112 to the internal lumen (reference numeral 124, see FIG. 7) of the sleeve 110 may be defined both in the first external surface 118 and in the second external surface 120. Also as shown, one or more of the openings 112 defined within the first external surface 118 may overlap in extent with one or more of the openings 112 defined within the second external surface 120. Defining openings 112 in both of the first external surface 118 and the second external surface 120 and the overlapping nature of the openings defined within the two surfaces 118, 120 decreases the likelihood that suction will be blocked by tissue drawn to the suction sleeve 110 by the applied vacuum and seal all of the openings. As best shown in the cutaway view FIG. 5, providing openings 112 in both surfaces 118 and 120 provides for an efficient flow of heated gasses and fluids by drawing them from both the radial direction relative to the shaft 104 (through openings 112 defined within the first surface 118 of the suction sleeve 110) and from the axial direction relative to the shaft 104 (through openings 112 defined within the second surface 120 of the suction sleeve 110).

Figure 6:
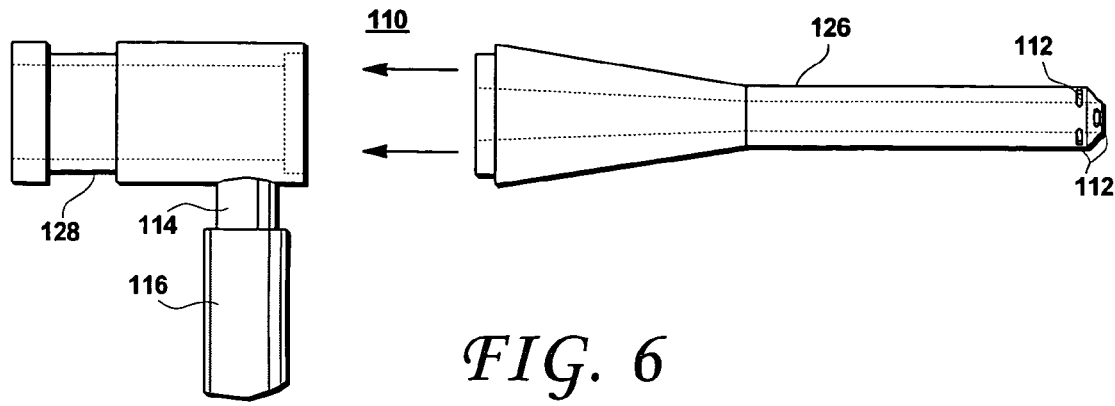
FIG. 6 is an exploded side view of the suction sleeve of FIGS. 1A.

FIG. 6 is an exploded side view of the suction sleeve of FIGS. 1A-B. As shown, according to an embodiment of the present invention, the suction sleeve 110 may include a proximal portion 128 and a distal portion 126. The proximal and distal portions 128, 126 may be configured to couple to one another, using an interference or snap-fit, for example. The proximal portion 128 may be configured to couple onto the handle 102 of the RF device, as shown in FIGS. 1A and 1B.

Figure 7:
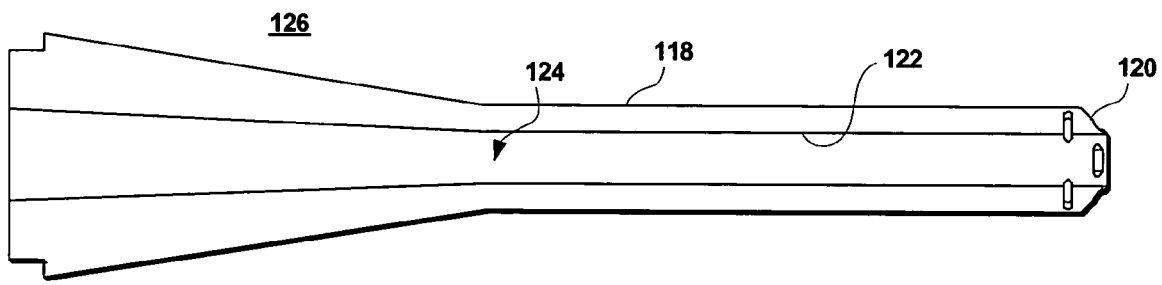
FIG. 7 is a cross-sectional side view of a portion of the suction sleeve shown in FIG. 3.

FIG. 7 is a side cross-sectional view of the distal portion 126 of the suction sleeve 110, according to an embodiment of the present invention. As shown, the second portion 126 may define a tapered profile to facilitate its travel within soft tissue (such as, for example, breast tissue). FIG. 7 also shows a portion of the internal lumen 124 of the suction sleeve 110, which internal lumen 124 communicates with the openings 112 defined within the first and/or second external surfaces 118, 120. In turn, the suction port 114 opens to the internal lumen 124, enabling suction applied thereto to draw gasses, fluids and/or other aspirates through the openings 112 and out through the suction port 114. Preferably, a balance should be struck in selecting the diameter of the internal lumen 124. The internal lumen 124 should be large enough to allow sufficient space between the shaft 104 to enable efficient suction of gasses and fluids, but not so large as to present to a cross-sectional area that would impede the advancement of the sleeve 110 within the tissue. Note that the suction port 114, the internal lumen 124 and the openings 112 may also be used to deliver gasses and/or fluids (e.g., lidocaine) to the excision site.

Figure 8:
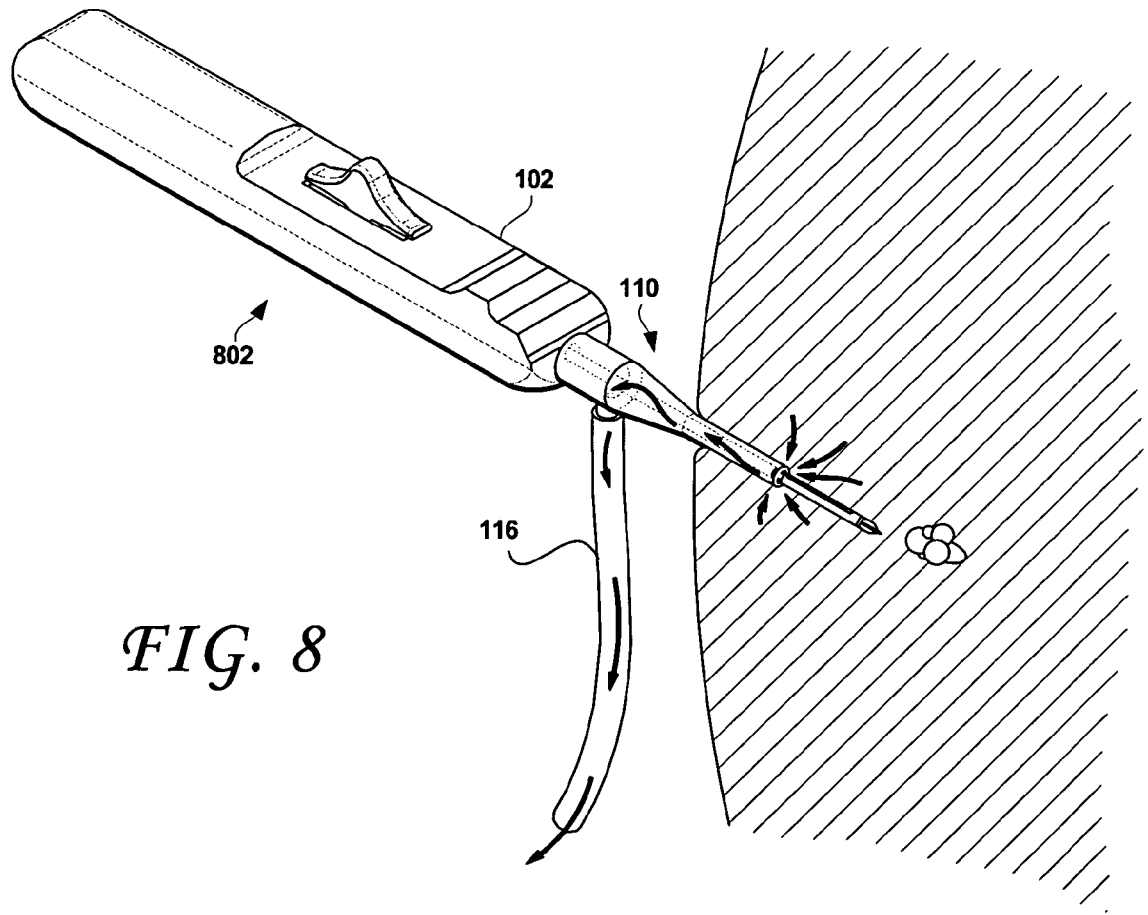
FIG. 8 shows an interventional device to which a suction sleeve according to an embodiment of the present invention is coupled, illustrating the manner in which smoke, fluids and/or other aspirates may be evacuated from a target site in the body during a biopsy or other procedure.

FIG. 8 shows an interventional device 802 to which a suction sleeve 110 according to an embodiment of the present invention is coupled, illustrating the manner in which smoke, fluids and/or other aspirates (collectively referenced by the curved arrows) may be evacuated from a target site in the body during a biopsy or other procedure. The suction applied to the suction port 114 through the vacuum line 116 may be turned on and off at will during the procedure.

Figure 9:
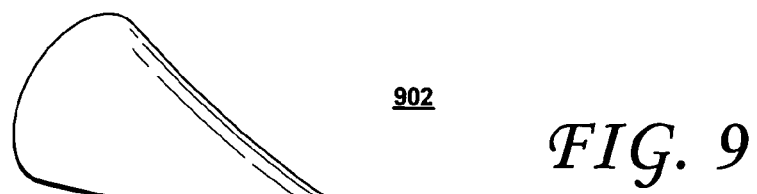
FIG. 9 is a perspective view of a combination introducer and suction sleeve, according to another embodiment of the present invention.
Figure 10:
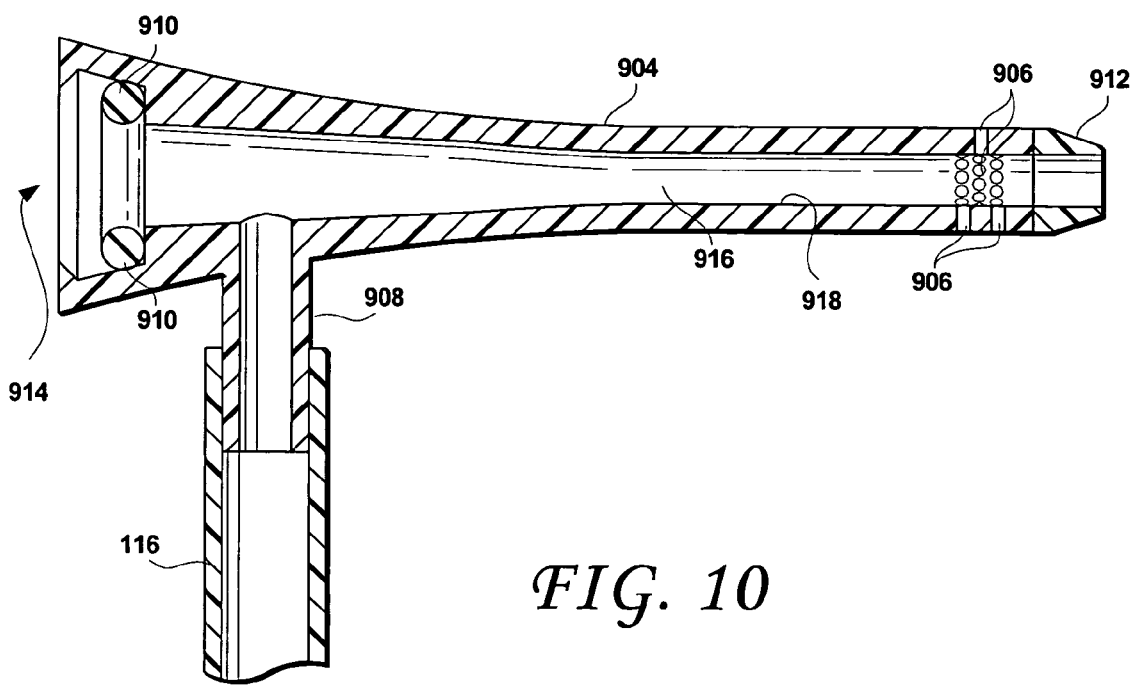
FIG. 10 is a side cross-sectional view of the combination introducer and suction sleeve of FIG. 9.
Figure 11:
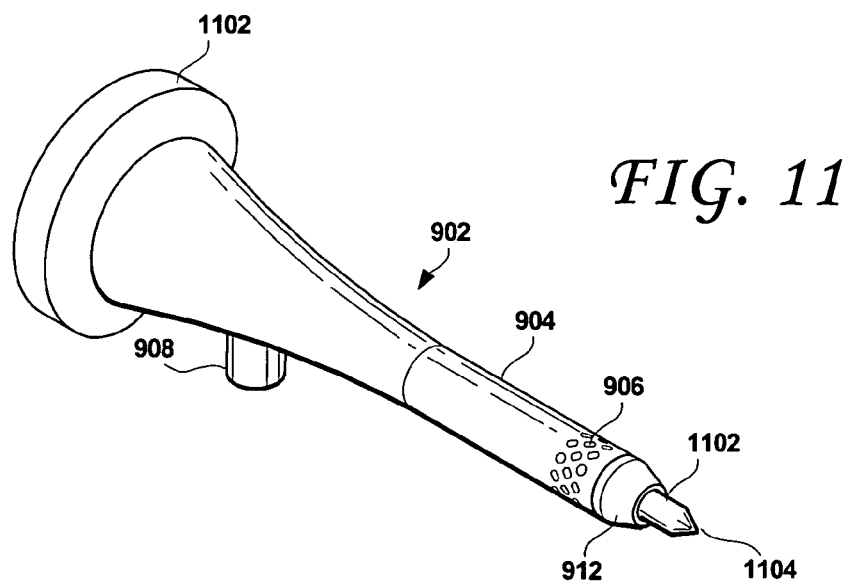
FIG. 11 is a perspective view of the combination introducer and suction sleeve of FIG. 9, with a trocar inserted therein.

FIG. 9 is a perspective view of a combination introducer and suction sleeve 902, according to another embodiment of the present invention. FIG. 10 is a side cross-sectional view thereof. Considering now FIGS. 9 and 10 collectively, the first external surface 904 of the combination introducer and suction sleeve 902 may have a generally tapered or funnel shape, in that it defines a relatively narrow diameter distal end and a relatively wider proximal end. Such a generally funnel or tapered shape eases the introduction of the device 802 within tissue. As with the suction sleeve of FIGS. 1A-8, the combination introducer and suction sleeve 902 includes a suction port 908 that opens to an internal lumen 916 defined by the internal surface 918. The combination introducer and suction sleeve 902 also includes a second external surface 912 that defines a tapered appearance. Defined within the first and/or second external surfaces 904, 912 are a plurality of openings 906 that open to the internal lumen 916. In FIGS. 9-11, only the first external surface 904 defines such openings 906, although the openings are not limited to this surface. The suction port 908 is configured to couple with a vacuum line, as shown at 116. The combination introducer and suction sleeve 902 may further include structures to couple to one or more devices, such as a trocar or an RF device such as, for example, a Bovie device or the device shown, for example, at reference numeral 802 in FIG. 8. Such coupling structure(s) may include, for example, a snap or interference fitting 914 and/or one or more O-rings, such as shown at 910.

Figure 12:
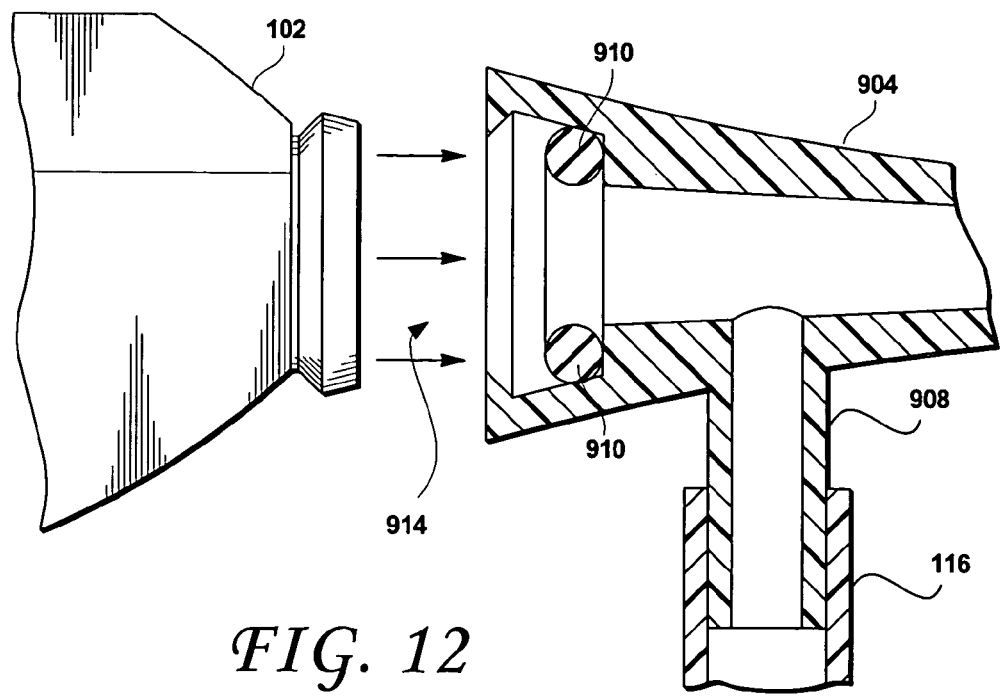
FIG. 12 is a side cross-sectional view of the combination introducer and suction sleeve of FIG. 9, illustrating exemplary structure with which the suction sleeve may attach to the interventional device.
Figure 13:
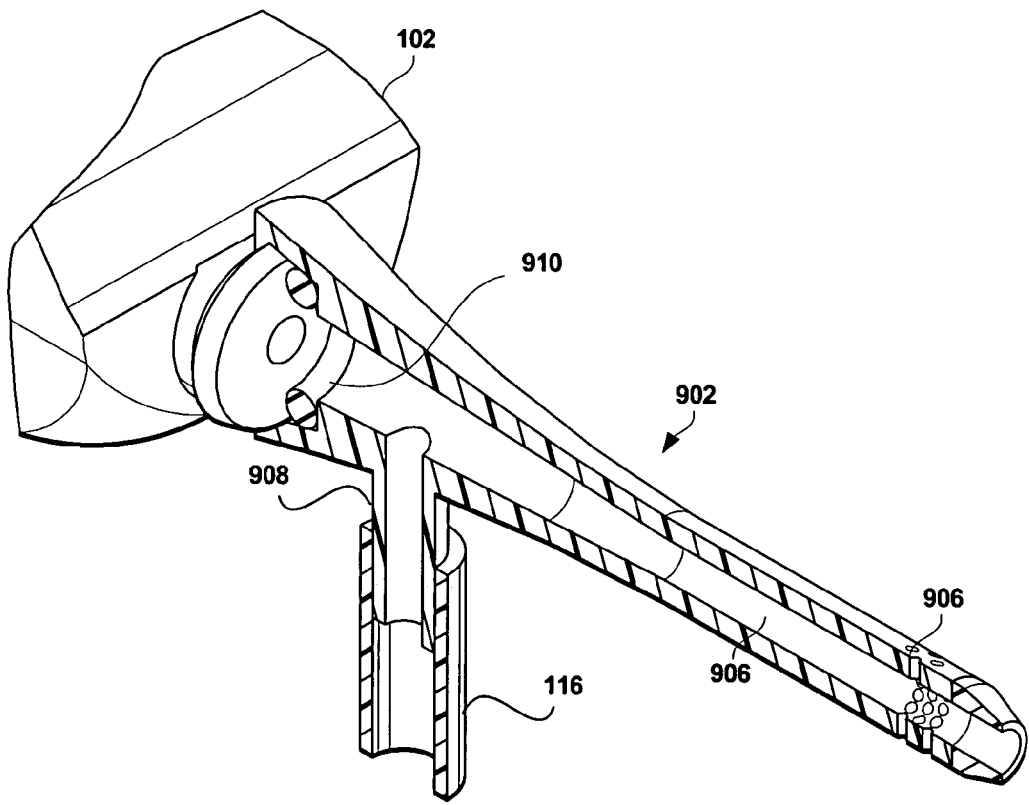
FIG. 13 is a perspective cross-sectional view of the combination introducer and suction sleeve, attached to an exemplary interventional device
Figure 14:
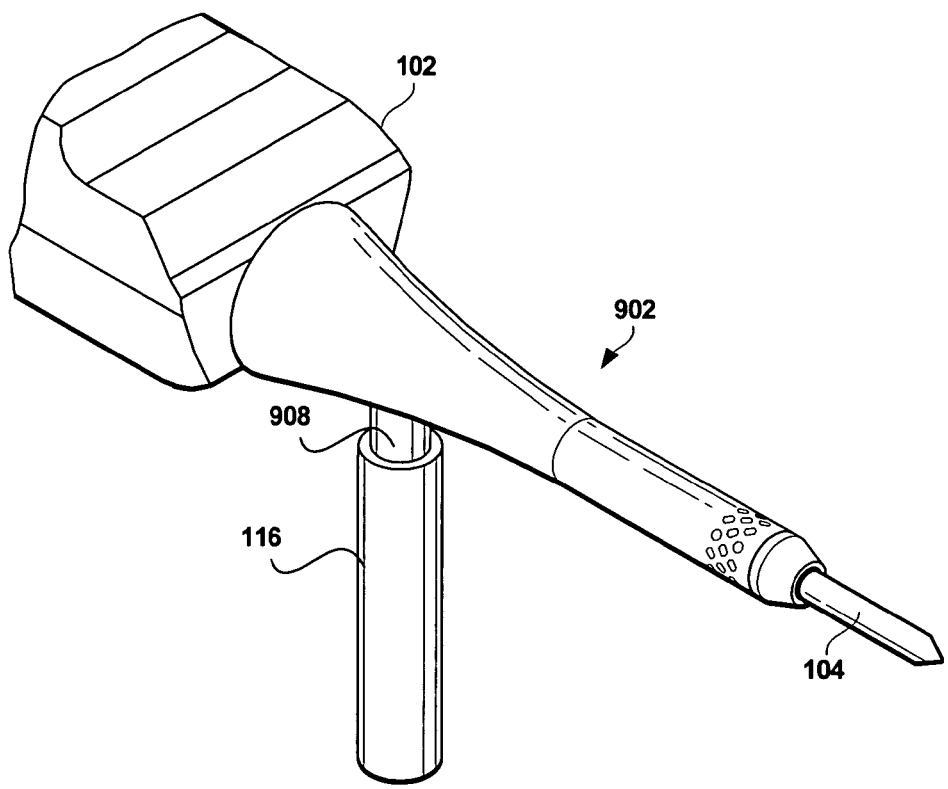
FIG. 14 is a perspective view of another embodiment of a suction sleeve according to the present invention, coupled to an exemplary interventional device.
Figure 15:
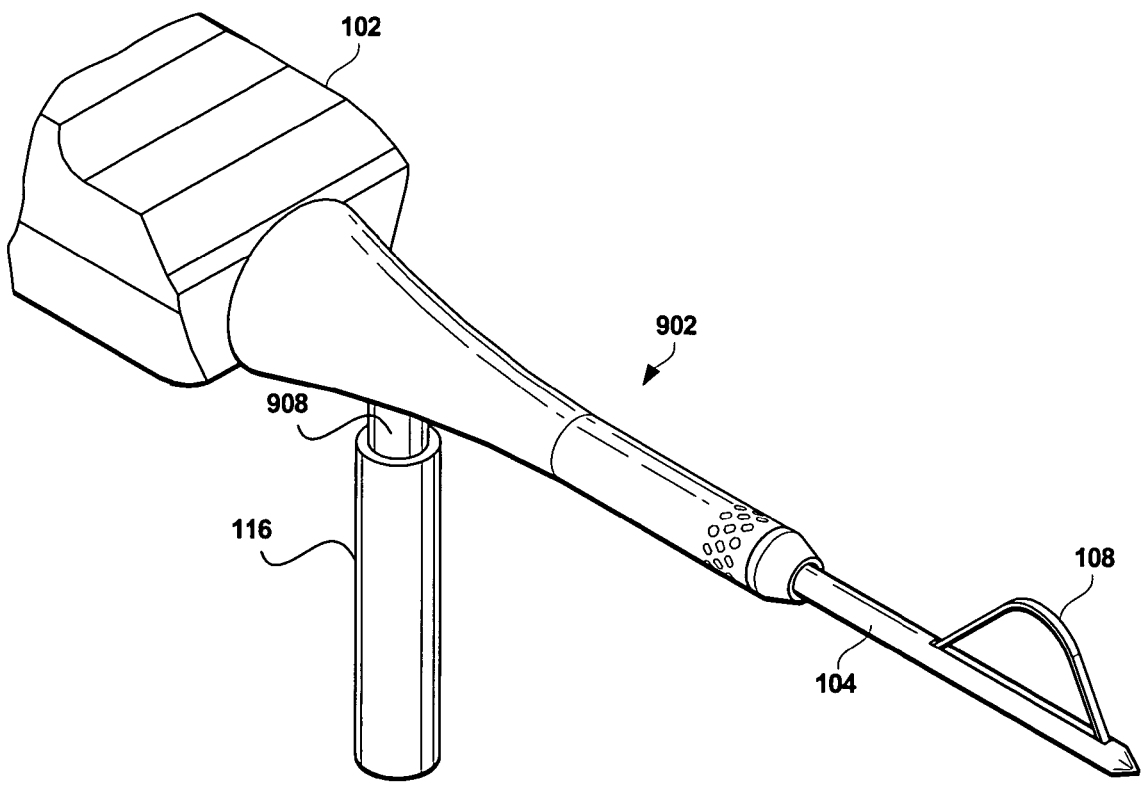
FIG. 15 is a perspective view of another embodiment of a suction sleeve according to the present invention, coupled to another exemplary interventional device.

FIG. 11 is a perspective view of the combination introducer and suction sleeve of FIG. 9, with a trocar 1102 inserted therein. According to an embodiment of the present invention, the trocar 1102 may be inserted into the combination introducer and suction sleeve 902 and the assembly may be packaged as a (preferably single use) unit. According to another embodiment of the present invention, a physician may utilize the assembly as follows:

1. An incision into tissue is made with a blade;
2. The physician then inserts the assembly including the trocar 1102 into the tissue and pushes the combination introducer and suction sleeve 902 into the tissue through the incision into position under or near the lesion or targeted site within the tissue. The pointed and/or sharp distal tip 1104 of the trocar 1102 and the tapered profile of the combination introducer and suction sleeve 902 aid the assembly's advancement within the tissue;
3. The trocar 1102 may then be removed from the combination introducer and suction sleeve 902 and a desired (excisional RF, for example) device may then be inserted therethrough, with the shaft thereof disposed within and protruding from the internal lumen 916;
4. The combination introducer and suction sleeve 902 may then be pulled back until it contacts, snaps and/or otherwise locks onto the device, as shown at FIGS. 12 and 13. In FIGS. 12 and 13, only the handle 102 of the device is shown, and the shaft 104 thereof is omitted for clarity of illustration. Examples of devices coupled to the combination introducer and suction sleeve 902 coupled thereto are shown in FIGS. 14 and 15;
5. A vacuum line, such as shown at 116, may then be attached to the suction port 908;
6. If needed, the device with the combination introducer and suction sleeve 902 attached thereto may then be repositioned at, near, under or within the target lesion, as desired. This repositioning may be carried out under ultrasound guidance, for example. The openings 906 may aid with the ultrasound visualization. The combination may include other features and/or markings to increase the visibility thereof under various imaging modalities, and
7. The physician may then continue with the intended procedure as per the instructions for use of the device utilized.

Alternatively, the trocar 1102 may be removed from the combination introducer and suction sleeve 902 and the desired RF device introduced and locked therein. The distal tip of the desired RF device protruding from the distal end of the combination introducer and suction sleeve 902 may then be used to reach the intended biopsy site.

Alternately still, a stopcock may be attached to the suction port 908 instead of the suction line 116 and one or more beneficial agents (e.g., antibiotics, fibrin, lidocaine) may be delivered to a target site through the openings 906.

The present combination vacuum sleeve and suction sleeve 902 may aid in positioning a biopsy or other interventional device where it is needed. For example, interventional devices that include a rather bulky or high-drag distal end may be readily positioned at the intended site by means of the introducer functionality of the combination 902. While the combination 902 is advantageous before the biopsy or other interventional procedure is started by easing the positioning of the biopsy instrument at or near the target site, it is also useful during the procedure itself, as it is effective in evacuating hot gasses and fluids from the biopsy cavity, thereby decreasing collateral tissue thermal damage. The same combination may then also be used to treat the cavity post-procedure by, for example, providing a ready-made pathway for the introduction of beneficial agents, compositions and/or cavity treatment devices to the cavity or lesion site.

Figure 16:
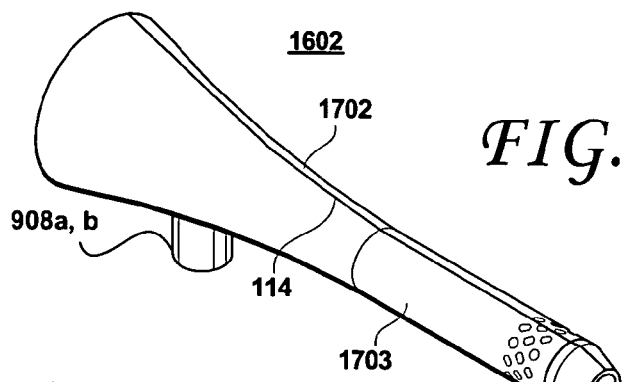
FIG. 16 shows a perspective view of another embodiment of the suction sleeve/introducer according to another embodiment of the present invention.
Figure 17:
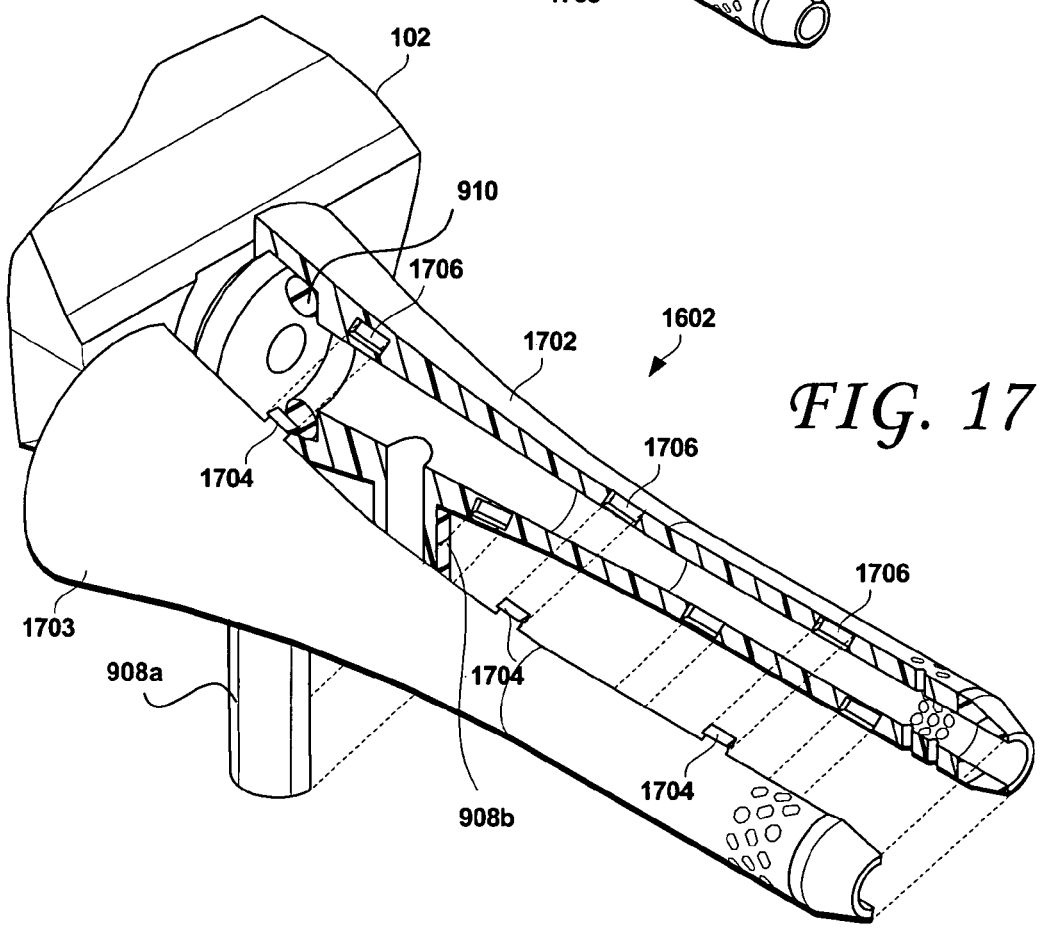
FIG. 17 is an exploded perspective view of the embodiment of the present suction sleeve/introducer shown in FIG. 16.
Figure 18:
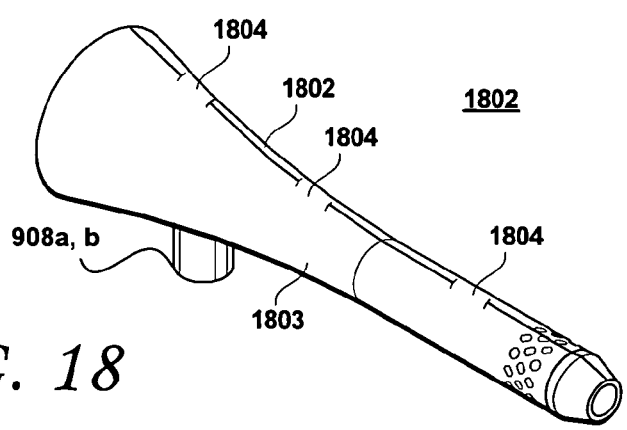
FIG. 18 is a perspective view of yet another embodiment of the suction sleeve/introducer according to the present invention.

FIG. 16 shows a perspective view and FIG. 17 shows an exploded perspective view of another embodiment of the combination introducer and suction sleeve 1602 according to another embodiment of the present invention. Considering now FIGS. 16 and 17 collectively, the combination introducer and suction sleeve 1602 is similar to the embodiment of FIGS. 9-15, but for the added feature of being formed of two halves 1702, 1703. As shown, the suction port of the combination introducer and suction sleeve 1602 is also split into two halves 908*a* and 908*b*. As shown in FIG. 17, the two halves 1702, 1703 of the combination introducer and suction sleeve 1602 may be coupled to one another via snap fit male and female features such as shown at 1704 and 1706, respectively. Alternatively, the two halves 1702, 1703 may mate to one another by means of an interference fit or other suitable mechanism. For example, FIG. 18 shows another embodiment of the present invention, in which the two halves of the combination introducer and suction sleeve 1802 are coupled to one another by integral hinges, such as shown at reference numerals 1804. For the embodiments shown in FIGS. 16-18, it may be expedient to locate the O-ring or other vacuum sealing structures on the handle 102 of the RF device. The embodiments of the suction sleeve shown in FIGS. 1-8 may be configured to include two mating suction sleeve halves, in the manner shown and described relative to FIGS. 16-18 or by means of other suitable mechanisms.

Figure 19:
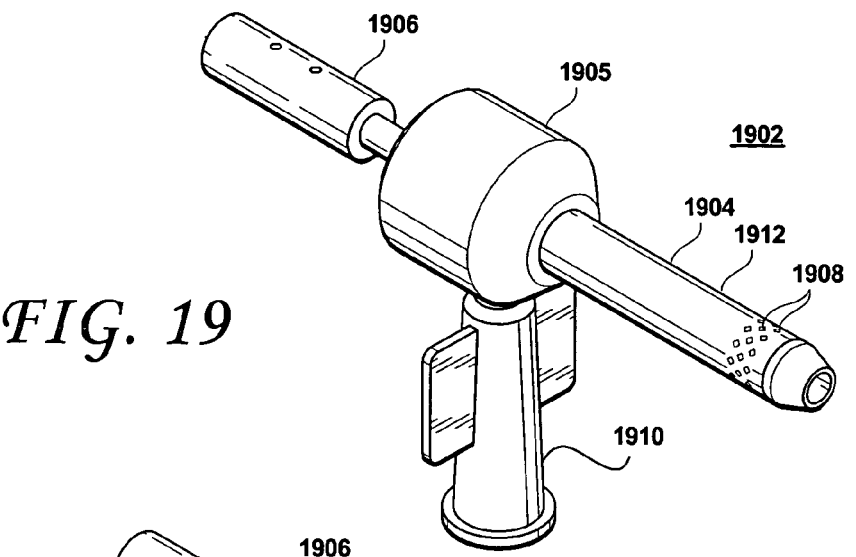
FIG. 19 is a perspective view of a suction sleeve according to a still further embodiment of the present invention, shown in a first configuration.
Figure 20:
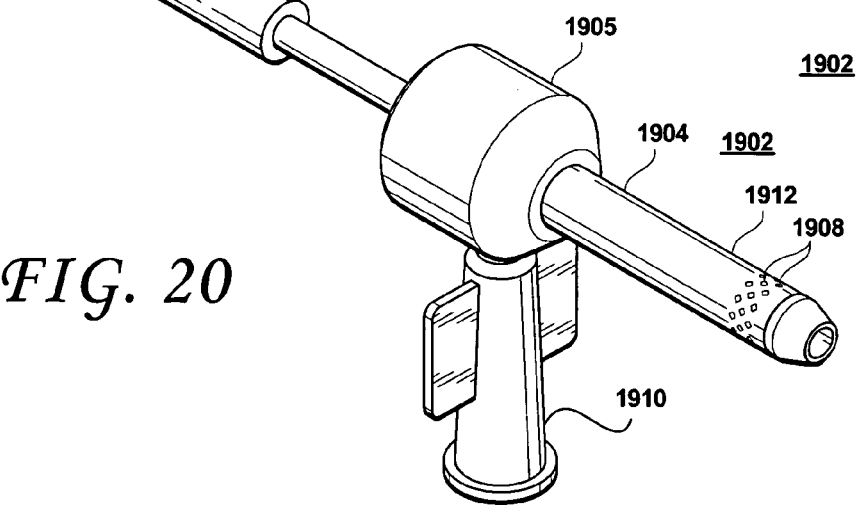
FIG. 20 is a perspective view of a suction sleeve according to a still further embodiment of the present invention, shown in a second configuration.

FIG. 19 is a perspective view of a suction sleeve 1902 according to a still further embodiment of the present invention, shown in a first configuration. FIG. 20 is a perspective view of the suction sleeve of FIG. 19, shown in a second configuration. As shown, the suction sleeve 1902 includes a first portion 1904, a center housing 1905 and a second portion 1906. According to this embodiment, the length of the suction sleeve 1902 may be varied from a first position in which the length of the suction sleeve 1902 is at a minimum, and selected second positions in which the length of the suction sleeve 1902 is greater than the minimum length.

Figure 21:
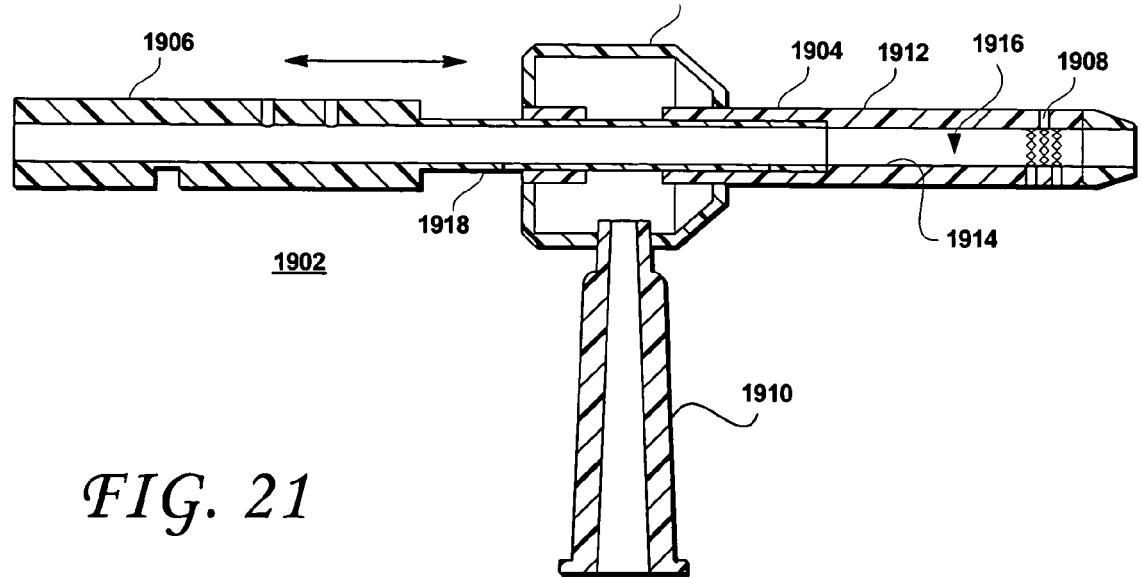
FIG. 21 is a side cross-sectional view of the suction sleeve of FIGS. 19 and 20.

As shown in FIGS. 19 and 20, the first external surface 1912 of the first portion 1904 may have a tapered shape to ease entry of the suction sleeve 1902 within tissue. The first external surface 1912 may define a plurality of openings 1908 near the distal end thereof. The first internal surface 1914 of the suction sleeve 1902 may define an internal lumen 1916 through which the shaft 104 of an RF device may be introduced. A suction port 1910 may be defined within the first portion or the center housing 1905 (as shown in FIGS. 19-21). A suction line (not shown) may be coupled to the suction port 1910. A second portion 1906 may be configured to slide (coaxially, for example) relative to the first portion 1904 (and/or the center housing 1905) to assume a first position in which the sleeve 1902 defines its minimum length and selected second positions (one of which is shown in FIG. 20) in which the length of the sleeve 1902 is greater than the aforementioned minimum length. Alternatively, the first portion 1904 could be configured to slide relative to the second portion 1906 and/or relative to the center housing 1905.

Figure 22:
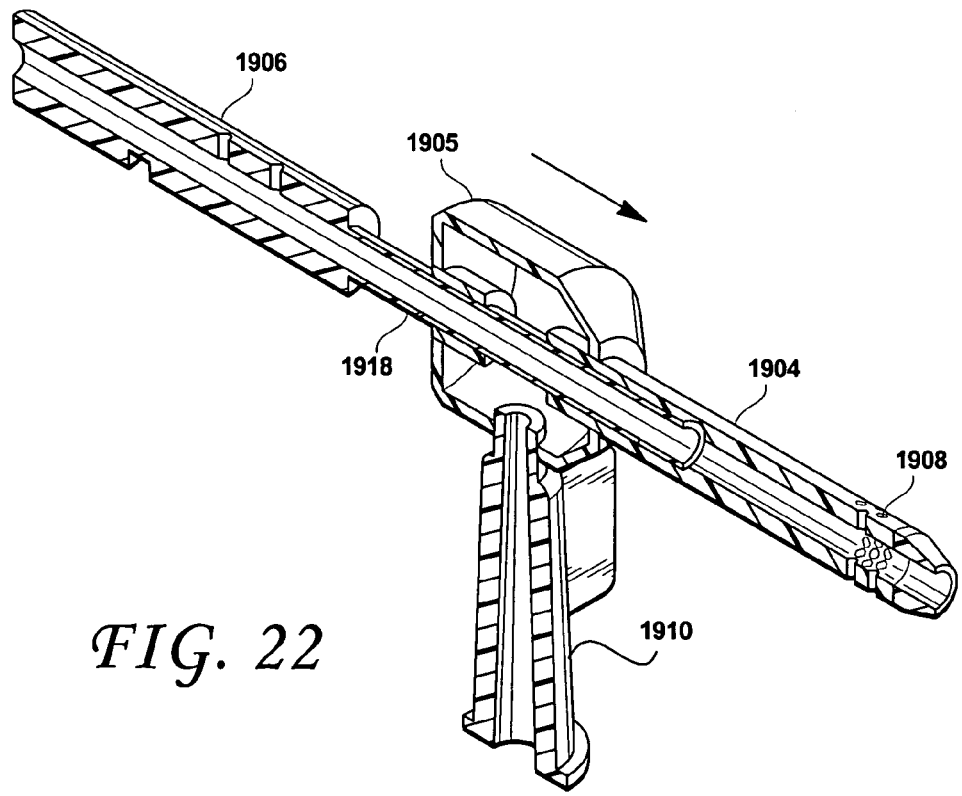
FIG. 22 is a perspective cross-sectional view of the suction sleeve of FIGS. 19 and 20, in the first configuration.
Figure 23:
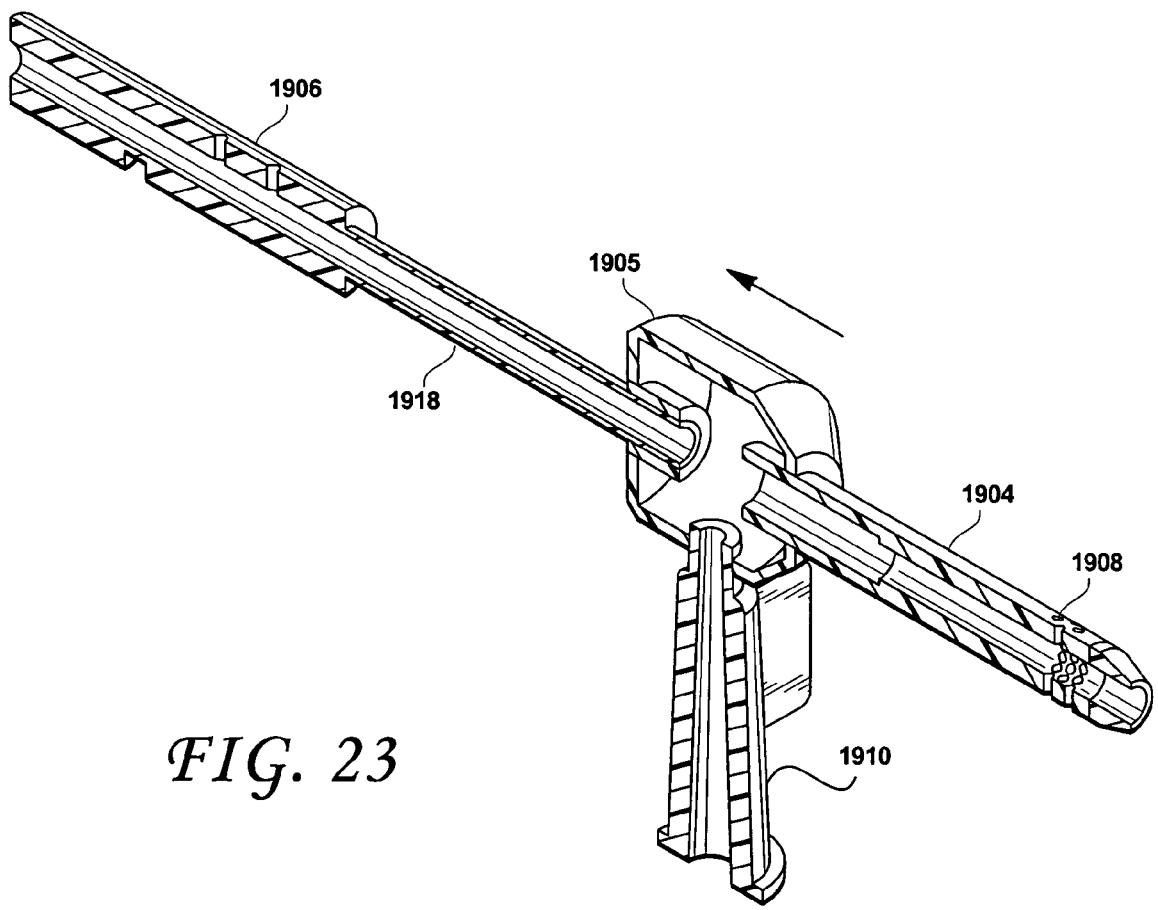
FIG. 23 is a perspective cross-sectional view of the suction sleeve of FIGS. 19 and 20, in a second (extended) configuration.

As shown in the side cross-sectional view of FIG. 21, an extension 1918 of the second portion 1906 of the suction sleeve 1902 may be configured to axially slide within the center housing 1905 and within the internal lumen 1916 of the first portion 1904. An opening may be defined in the second portion 1906 to enable gasses, fluids and other aspirates to be sucked into the suction port 1910. Alternatively, the sleeve 1902 may be configured so as to enable suction only when the sleeve 1902 is in its second, extended configuration as shown in FIG. 23. FIGS. 22 and 23 show the embodiment of FIGS. 19-21 in the first configuration in which the length of the sleeve 1902 is at its minimum and in the second configuration in which the length of the sleeve 1902 is at its maximum, respectively.

Figure 24:
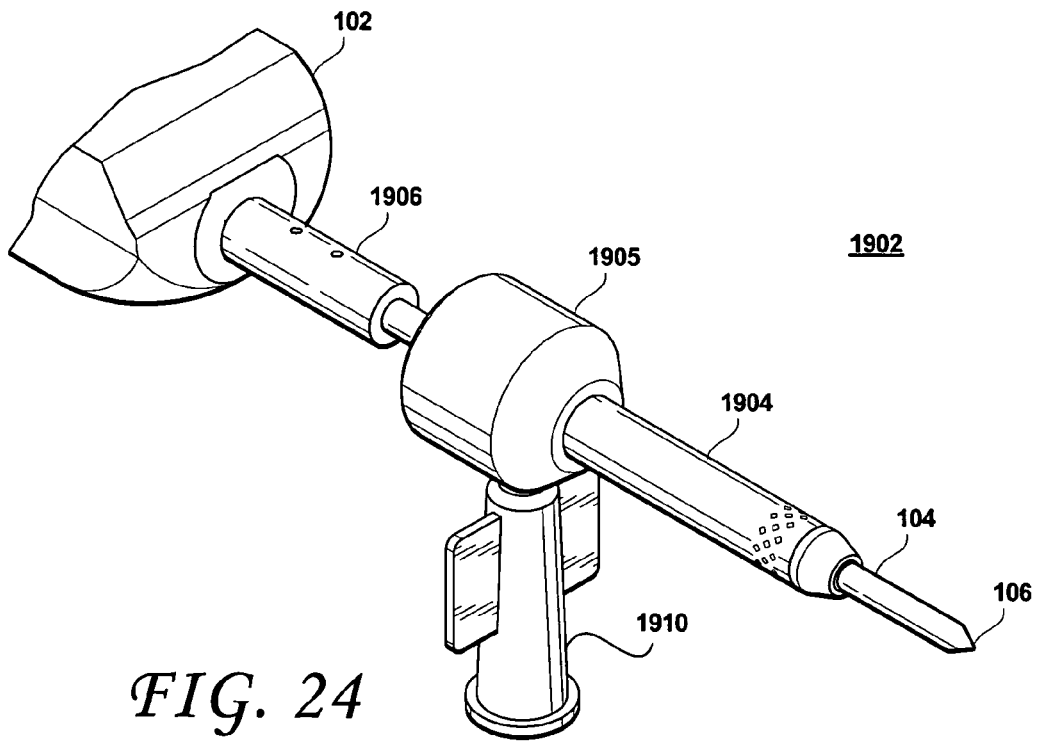
FIG. 24 shows the suction sleeve of FIGS. 19 and 20, coupled to an exemplary electrosurgical device.
Figure 25:
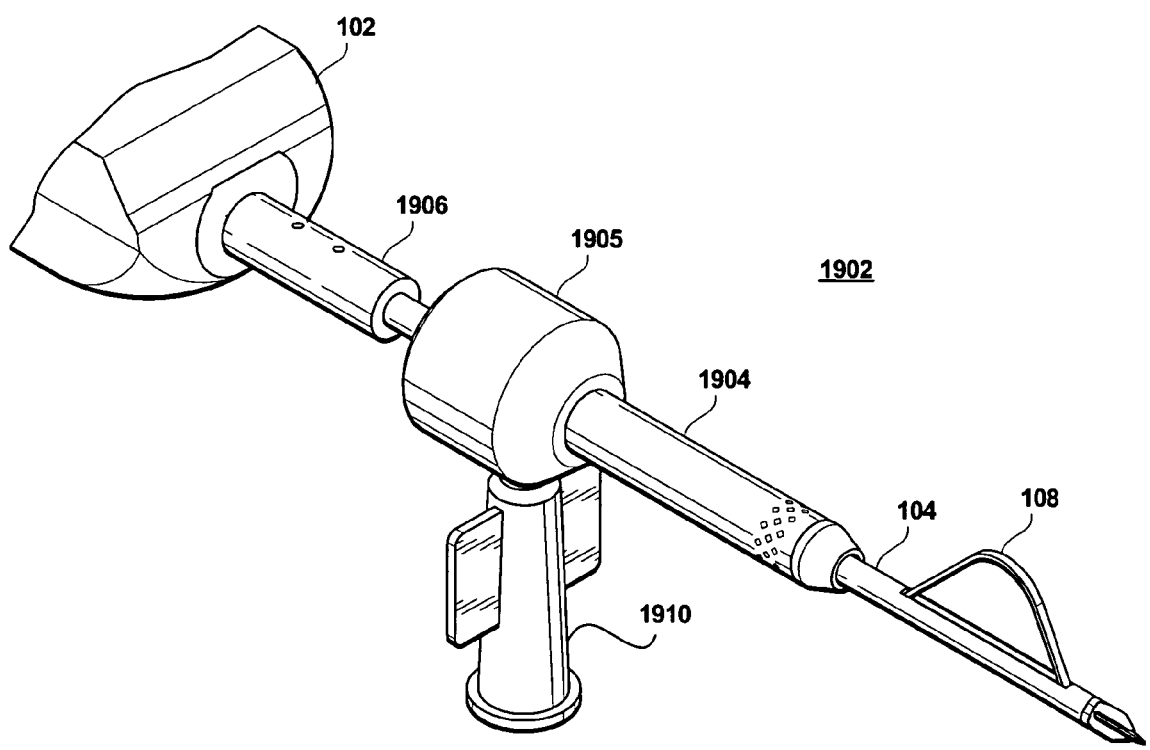
FIG. 25 shows the suction sleeve of FIGS. 19 and 20, coupled to another exemplary electrosurgical device.

FIGS. 24 and 25 show the suction sleeve 1902 coupled to two exemplary RF devices. The suction sleeve 1902 of FIG. 24 is coupled to an RF device similar to a Bovie pencil, whereas the suction sleeve of FIG. 25 is coupled to an RF excisional device that includes a bowing RF blade 108, such as available from the present assignee Rubicor Medical, Inc. of Redwood City Calif. In both cases, the distal end of the shaft 104 is inserted within and protrudes from the internal lumen 1916 of the suction sleeve 1902. The second portion 1906 may (but need not) be coupled to the handle 102 of the RF device. For example, the second portion 1906 may be coupled to the handle by a snap fitting, an interference fit or by other suitable mechanisms.

Figure 26:
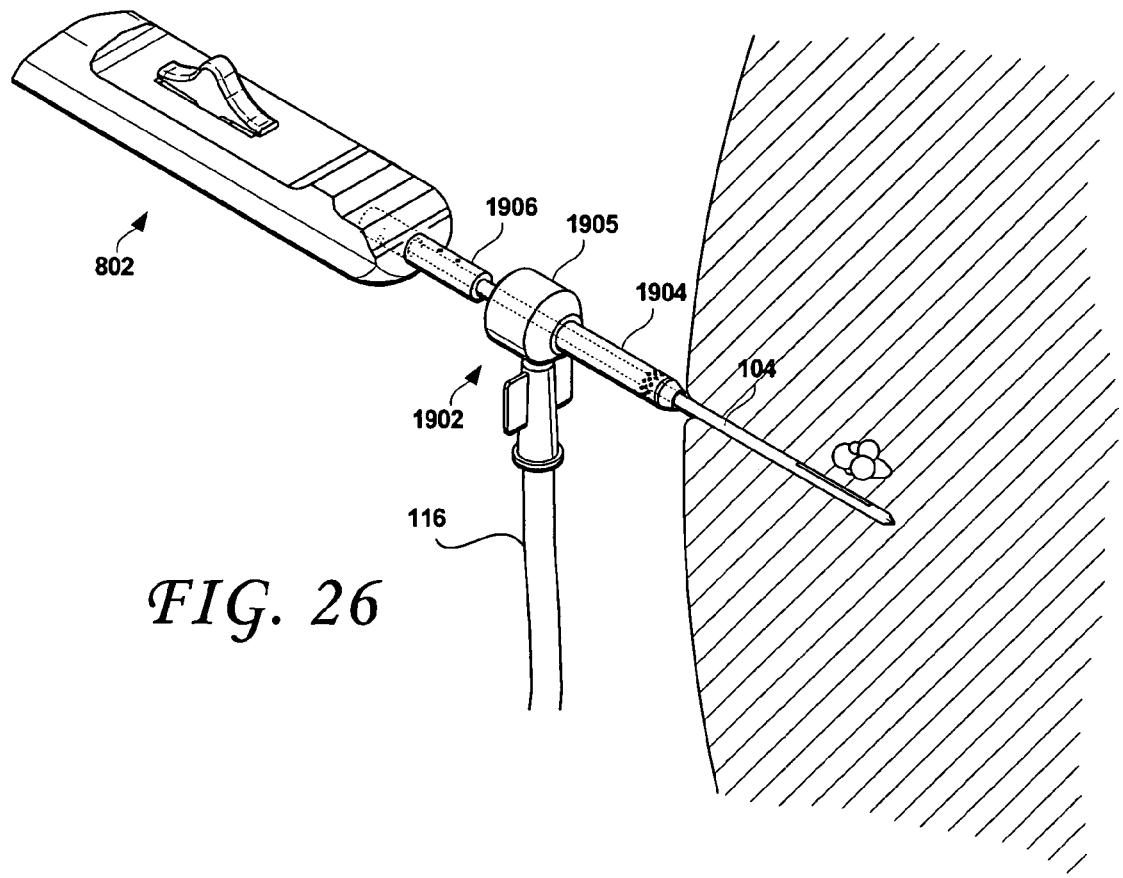
FIG. 26 shows an interventional device to which the suction sleeve of FIGS. 19 and 20 has been coupled, in use.
Figure 27:
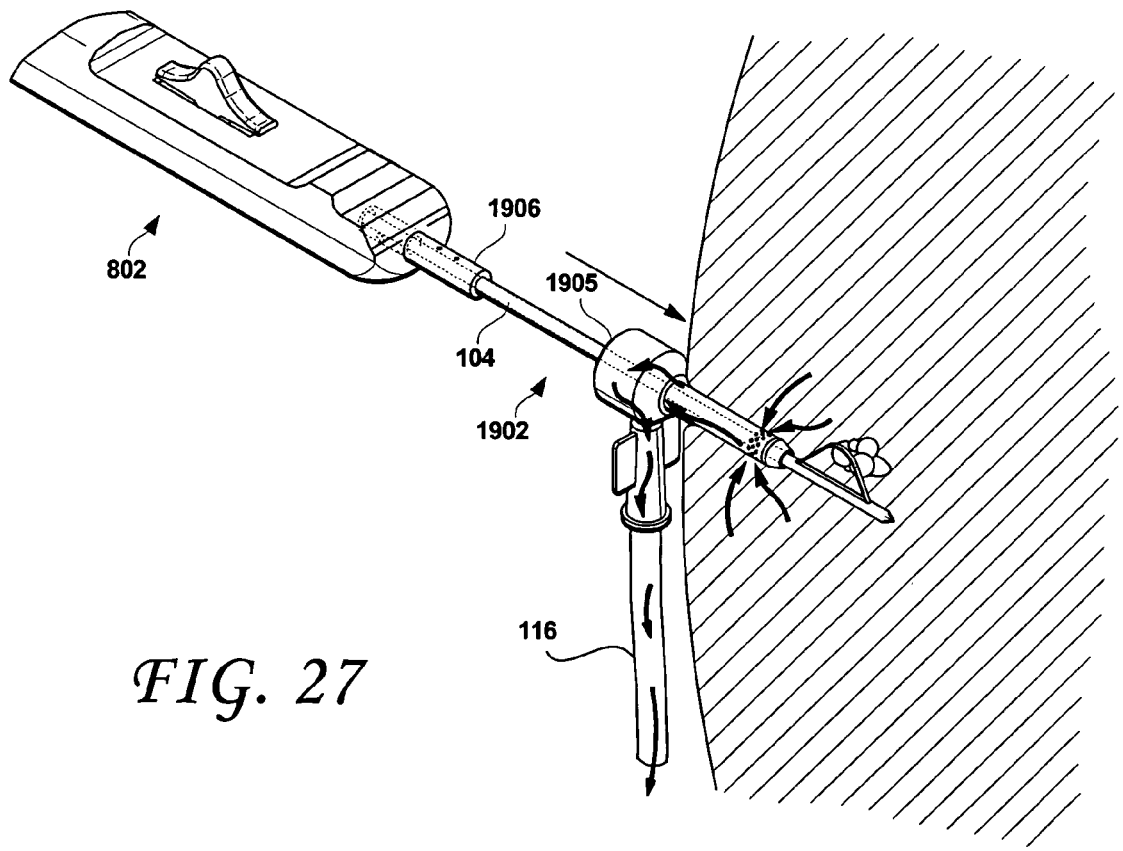
FIG. 27 shows the interventional device of FIG. 26 in use, and illustrates further aspects thereof.
Figure 28A:
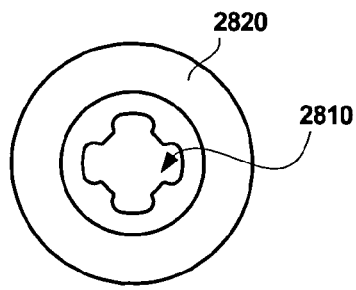
FIG. 28A is a front view of the distal end of a suction sleeve according to another embodiment of the present invention.
Figure 28B:
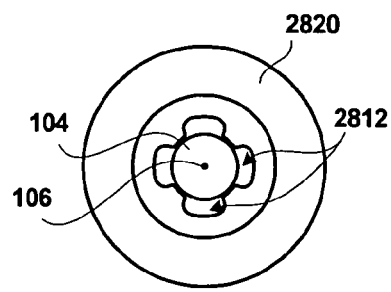
FIG. 28B shows the embodiment of FIG. 28A, with an excisional device inserted therein, to illustrate the manner in which the distal opening allows suction.

FIGS. 26 and 27 show the assembly of FIG. 25 in use. The suction sleeve 1902 is coupled to the handle 102 of an RF device 802. As shown in FIG. 26, the shaft 104 may be inserted into the tissue through an incision, with the suction sleeve 1902 in its first configuration. In such a configuration, the first portion 1904 of the suction sleeve 1902 may be maintained outside of the tissue, thereby easing the initial entry of the RF device through the tissue. After the distal portion of the shaft has been positioned within the tissue to the physician's satisfaction (adjacent a target lesion, for example), the second portion 1906 being otherwise stationary, the physician may slide the first portion 1904 (by manually grasping the center housing 1905, for example) into the tissue such that the distal end thereof is adjacent the RF device's work element (in this case, the bowing RF blade). In this configuration, hot gasses and fluids generated incident to the RF cutting and coagulation action of the RF device's work element may be evacuated through the openings 1908, through the internal lumen 1916, through the suction port 1910 and out through the suction line 116 coupled to the suction port 1910.

Figure 29:
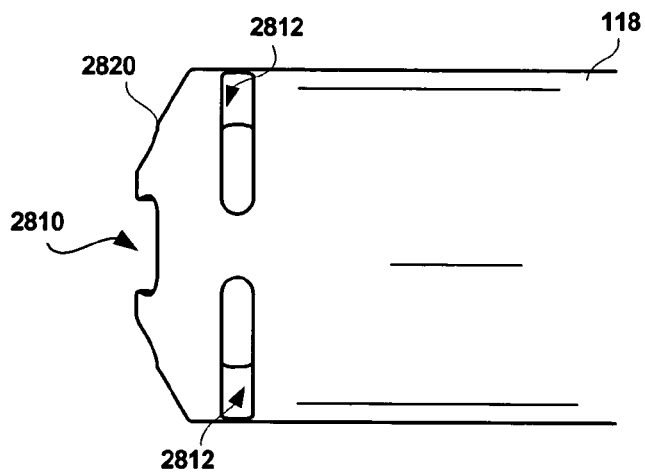
FIG. 29 is a partial side view of the embodiment of the suction sleeve shown in FIGS. 28A and 28B.
Figure 30:
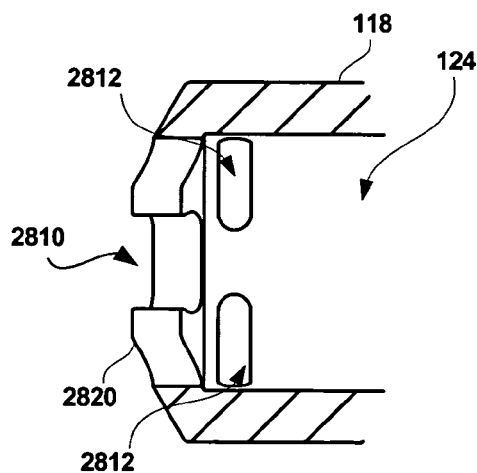
FIG. 30 is a side cross sectional view of the embodiment of the present suction sleeve shown in FIG. 29

FIGS. 28A, 28B, 29 and 30 illustrate aspects of another embodiment of the present suction sleeve. Whereas the distal opening of the suction sleeve of FIGS. 1-27 is circular in shape, the present inventions are not so limited. Indeed, the distal end of the embodiment of FIGS. 28A-30 includes a surface or surfaces 2820 that define an opening 2820 having a generally cloverleaf shape, shown at reference 2810. This opening may be described as a circular shape having a number of side lobe openings. Such a shape enables the excisional device 104 to be securely held and centered within the suction sleeve, yet allows suction to occur not only at the sides of the suction sleeve, but also at the distal tip thereof, through the side lobe openings 2812. As shown in FIGS. 29 and 30, the suction sleeve may also include a number of openings 2812 defined within the exterior surface 118, to further promote suction and evacuation of aspirates within the cavity. It is to be understood that the openings defined at or near the distal end of the present suction sleeve may have other shapes than those shown and described herein. Other variations may occur to those of skill in this art, and all such variations or modifications are deemed to fall within the spirit and scope of the inventions shown, described and claimed herein.

While the foregoing detailed description has described preferred embodiments of the present invention, it is to be understood that the above description is illustrative only and not limiting of the disclosed invention. Thus, the present invention should be limited only by the claims as set forth below.

What is claimed is:

1. A soft tissue interventional device, comprising:
   a handle;
   a shaft defining a proximal end and a distal end, the proximal end being coupled to the handle;
   a lone electrode coupled near the distal end of the shaft, the electrode being configured to be energized with RF energy to cut tissue, and
   a suction sleeve, the suction sleeve and the shaft being freely rotatable relative to one another such that the shaft is freely rotatable within a stationary suction sleeve and such that the suction sleeve is freely rotatable about a stationary shaft, the suction sleeve including an outer surface and an inner surface that faces and is disposed coaxially around the shaft so as to define an interstitial space between the inner surface and the shaft, the suction sleeve being disposed only between the proximal end of the shaft and the electrode, the outer surface of the suction sleeve defining a plurality of openings that are in fluid communication with the interstitial space, the suction sleeve defining a suction port adjacent the proximal end of the shaft, the suction port being disposed at a non-zero angle relative to a longitudinal axis of the shaft and being configured to enable liquid and gases collected near the electrode to be sucked into the interstitial space through at least one of the plurality of openings and to be evacuated out through the suction port.

2. The device of claim 1, wherein the suction sleeve defines a circumference around the shaft and wherein the plurality of openings is defined around the circumference of the suction sleeve.

3. The device of claim 2, wherein the plurality of openings overlap around the circumference of the suction sleeve.

4. The device of claim 1, wherein the suction sleeve defines a first external surface and a second external surface disposed at a non-zero angle relative to first external surface, and wherein at least one of the plurality of openings is defined within the first external surface and at least one of the plurality of openings is defined within the second external surface.

5. The device of claim 4, wherein the at least one of the plurality of openings defined within the first external surface overlaps in extent with the at least one of the plurality of openings defined within the second external surface.

6. The device of claim 1, wherein at least one of the plurality of openings defines a generally cloverleaf shape.

7. The device of claim 1, wherein the sleeve includes an inner surface that defines an interior sleeve lumen dimensioned so as to allow the shaft to freely rotate therethrough.

8. The device of claim 7, wherein the plurality of openings are open to the interior sleeve lumen.

9. The device of claim 7, wherein the interior sleeve lumen is dimensioned so as to allow free passage of liquids and gases through the plurality of openings and out the suction port.

10. The device of claim 1, wherein the suction sleeve is configured to be removable from the shaft.

11. The device of claim 1, wherein the suction sleeve is configured to be positioned on the shaft without decoupling the shaft from the handle.

12. The device of claim 1, wherein the suction sleeve is at least partially transparent.

13. The device of claim 1, wherein the sleeve comprises a first portion and a second portion, the second portion being configured to slide coaxially relative to the first portion to assume a first position in which the sleeve has a first length and second positions in which the length of the sleeve is greater than the first length.

14. The device of claim 13, wherein the second portion telescopes with the first portion.

15. A method for cutting a specimen of soft tissue, comprising the steps of:
providing a device including a handle; a shaft defining a proximal end and a distal end, the proximal end being coupled to the handle; a lone electrode coupled near the distal end of the shaft, the electrode being configured to be energized with RF energy to cut tissue, and a suction sleeve, the suction sleeve and the shaft being freely rotatable relative to one another such that the shaft is freely rotatable within a stationary suction sleeve and such that the suction sleeve is freely rotatable about a stationary shaft, the suction sleeve including an outer surface and an inner surface that faces and is disposed coaxially around the shaft so as to define an interstitial space between the inner surface and the shaft, the suction sleeve being disposed only between the proximal end of the shaft and the electrode, the outer surface of the suction sleeve defining a plurality of openings that are in fluid communication with the interstitial space, the suction sleeve defining a suction port adjacent the proximal end of the shaft, the suction port being disposed at a non-zero angle relative to a longitudinal axis of the shaft and being configured to enable liquid and gases collected near the electrode to be sucked into the interstitial space through at least one of the plurality of openings and to be evacuated out through the suction port;
inserting the device in the soft tissue;
applying RF energy to the electrode;
cutting the tissue specimen using the energized electrode, and
applying suction to the suction port during the cutting step.

16. A soft tissue interventional device, comprising:
a handle;
a shaft defining a proximal end and a distal end, the proximal end being coupled to the handle;
a single work element coupled near the distal end of the shaft, the work element being configured to be energized with RF energy to cut tissue, and
a suction sleeve, the suction sleeve and the shaft being freely rotatable relative to one another such that the shaft is freely rotatable within a stationary suction sleeve and such that the suction sleeve is freely rotatable about a stationary shaft, the suction sleeve including an inner surface that faces and is disposed coaxially around the shaft so as to define an interstitial space between the inner surface and the shaft, the suction sleeve being disposed only between the proximal end of the shaft and the single work element, the suction sleeve defining a suction port adjacent the proximal end of the shaft, the suction port being disposed at a non-zero angle relative to a longitudinal axis of the shaft, the suction sleeve further defining a plurality of openings in fluid communication with the interstitial space such that liquid and gases collected near the work element are sucked into the interstitial space through the plurality of openings and are evacuated through the suction port, the suction sleeve further defining a first external surface in which at least one of the plurality of openings is defined and a second external surface, disposed at a non-zero angle relative to the first external surface, in which at least one of the plurality of openings is defined.

17. The device of claim 16, wherein the suction sleeve defines a circumference around the shaft and wherein the plurality of openings is defined around the circumference of the suction sleeve.

18. The device of claim 17, wherein the plurality of openings overlap around the circumference of the suction sleeve.

19. The device of claim 16, wherein the at least one of the plurality of openings defined within the first external surface overlaps in extent with the at least one of the plurality of openings defined within the second external surface.

20. The device of claim 16, wherein at least one of the plurality of openings defines a generally cloverleaf shape.

21. The device of claim 16, wherein the suction sleeve is configured to be freely rotatable about the shaft.

22. The device of claim 16, wherein the inner surface defines an interior sleeve lumen dimensioned so as to allow the shaft to freely rotate therethrough.

23. The device of claim 22, wherein the plurality of openings are open to the interior sleeve lumen.

24. The device of claim 22, wherein the interior sleeve lumen is dimensioned so as to allow free passage of liquids and gases through the plurality of openings and out the suction port.

25. The device of claim 16, wherein the suction sleeve is configured to be removable from the shaft.

26. The device of claim 16, wherein the suction sleeve is configured to be positioned on the shaft without decoupling the shaft from the handle.

27. The device of claim 16, wherein the suction sleeve is at least partially transparent.

28. The device of claim 16, wherein the sleeve comprises a first portion and a second portion, the second portion being configured to slide coaxially relative to the first portion to assume a first position in which the sleeve has a first length and second positions in which the length of the sleeve is greater than the first length.

29. The device of claim 28, wherein the second portion telescopes with the first portion.

30. A soft tissue interventional device, comprising:
a handle;
a shaft defining a proximal end and a distal end, the proximal end being coupled to the handle;
a single work element coupled near the distal end of the shaft, the work element being configured to be energized with RF energy to cut tissue, and
a suction sleeve including a first portion, a second portion and an inner surface that faces and is disposed coaxially around the shaft so as to define an interstitial space between the inner surface and the shaft, the suction sleeve being disposed only between the proximal end of the shaft and the single work element, the suction sleeve defining a suction port and being configured to enable suction of liquid and gases collected near the work element into the interstitial space and out through the suction port, the second portion being configured to telescope within the first portion such that the second portion is configured to slide coaxially relative to the first portion to assume a first position in which the sleeve has a first length and a second position in which the length of the sleeve is greater than the first length.

31. The device of claim 30, further comprising a plurality of openings defined in the suction sleeve, configured such that the liquid and gases are sucked into the interstitial space through the plurality of openings and are evacuated out of the suction sleeve through the suction port.

32. The device of claim 31, wherein the suction sleeve defines a circumference around the shaft and wherein the plurality of openings is defined around the circumference of the suction sleeve.

33. The device of claim 32, wherein the plurality of openings overlap around the circumference of the suction sleeve.

34. The device of claim 31, wherein the suction sleeve defines a first external surface and a second external surface disposed at a non-zero angle relative to first external surface, and wherein at least one of the plurality of openings is defined within the first external surface and at least one of the plurality of openings is defined within the second external surface.

35. The device of claim 34, wherein the at least one of the plurality of openings defined within the first external surface overlaps in extent with the at least one of the plurality of openings defined within the second external surface.

36. The device of claim 31, wherein at least one of the plurality of openings defines a generally cloverleaf shape.

37. The device of claim 30, wherein the suction port is defined within the suction sleeve adjacent the proximal end of the shaft.

38. The device of claim 30, wherein the suction sleeve is configured to be freely rotatable about the shaft.

39. The device of claim 30, wherein the inner surface defines an interior sleeve lumen dimensioned so as to allow the shaft to freely rotate therethrough.

40. The device of claim 39, wherein the plurality of openings are open to the interior sleeve lumen.

41. The device of claim 39, wherein the interior sleeve lumen is dimensioned so as to allow free passage of liquids and gases through the plurality of openings and out the suction port.

42. The device of claim 30, wherein the suction sleeve is configured to be removable from the shaft.

43. The device of claim 30, wherein the suction sleeve is configured to be positioned on the shaft without decoupling the shaft from the handle.

44. The device of claim 30, wherein the suction sleeve is at least partially transparent.

* * * * *